(12) United States Patent  
Stone et al.

(10) Patent No.: US 8,057,482 B2  
(45) Date of Patent: Nov. 15, 2011

(54) SURGICAL ORIENTATION DEVICE AND METHOD

(75) Inventors: A. Curt Stone, Aspinwall, PA (US);  
Joseph F. Russial, Pittsburgh, PA (US)

(73) Assignee: OrthAlign, Inc., Aliso Viejo, CA (US)

( * ) Notice: Subject to any disclaimer, the term of this patent is extended or adjusted under 35 U.S.C. 154(b) by 903 days.

(21) Appl. No.: 10/864,085

(22) Filed: Jun. 9, 2004

(65) Prior Publication Data  
US 2005/0021044 A1 Jan. 27, 2005

Related U.S. Application Data

(60) Provisional application No. 60/476,998, filed on Jun. 9, 2003.

(51) Int. Cl.  
*A61B 17/58* (2006.01)  
*A61B 17/60* (2006.01)  
*A61B 19/00* (2006.01)  
*A61B 5/103* (2006.01)  
*A61B 5/117* (2006.01)  
*A61F 2/00* (2006.01)  
*G01P 7/00* (2006.01)  
*G01P 9/00* (2006.01)  
*G01P 15/14* (2006.01)  
*G01C 9/00* (2006.01)  
*G01C 17/00* (2006.01)  
*G01C 19/00* (2006.01)

(52) U.S. Cl. .......... 606/102; 606/88; 606/130; 600/587; 73/503; 73/504.02; 702/153

(58) Field of Classification Search .................. 600/587, 600/300, 595; 606/102, 130, 88, 86 R–86 B, 606/87, 89, 91; 73/1.77, 504.01–504.16; 33/318, 321–323, 328–330, 365, 366.11–366.14; 702/150–154  
See application file for complete search history.

(56) References Cited

U.S. PATENT DOCUMENTS

| 3,174,080 | A | * | 3/1965 | Scott .............................. 361/167 |
| 4,349,018 | A | | 9/1982 | Chambers |
| 4,459,985 | A | | 7/1984 | McKay et al. |
| 4,501,266 | A | | 2/1985 | McDaniel |

(Continued)

FOREIGN PATENT DOCUMENTS

CA 2 241 359 A1 12/1999

(Continued)

OTHER PUBLICATIONS

Goniometer, AllHeart.com, 2004, p. 1 (website: http://allheart.com/allheart.

(Continued)

*Primary Examiner* — Max Hindenburg  
*Assistant Examiner* — John Pani  
(74) *Attorney, Agent, or Firm* — Knobbe, Martens, Olson & Bear LLP

(57) ABSTRACT

A device for detecting and measuring a change in angular position with respect to a reference plane is useful in surgical procedures for orienting various instruments, prosthesis, and implants with respect to anatomical landmarks. One embodiment of the device uses three orthogonal rate sensors, along with integrators and averagers, to determine angular position changes using rate of change information. A display provides position changes from a reference position. Various alignment guides are useful with surgical instruments to obtain a reference plane.

13 Claims, 22 Drawing Sheets

U.S. PATENT DOCUMENTS

| | | | |
|---|---|---|---|
| 4,518,855 A * | 5/1985 | Malak | 356/141.3 |
| 4,524,766 A | 6/1985 | Petersen | |
| 4,529,348 A | 7/1985 | Johnson et al. | |
| 4,567,885 A | 2/1986 | Androphy | |
| 4,621,630 A | 11/1986 | Kenna | |
| 4,646,729 A | 3/1987 | Kenna | |
| 4,716,894 A | 1/1988 | Lazzeri et al. | |
| 4,718,078 A * | 1/1988 | Bleidorn et al. | 700/256 |
| 4,738,253 A | 4/1988 | Buechel et al. | |
| 4,759,350 A | 7/1988 | Dunn et al. | |
| 4,938,762 A | 7/1990 | Wehrli | |
| 4,944,760 A | 7/1990 | Kenna | |
| 4,952,213 A | 8/1990 | Bowman et al. | |
| 5,002,547 A | 3/1991 | Poggie et al. | |
| 5,053,037 A | 10/1991 | Lackey | |
| 5,065,612 A * | 11/1991 | Ooka et al. | 73/1.77 |
| 5,129,908 A | 7/1992 | Petersen | |
| 5,213,112 A | 5/1993 | Niwa et al. | |
| 5,249,581 A | 10/1993 | Horbal et al. | |
| 5,251,127 A | 10/1993 | Raab | |
| 5,279,309 A | 1/1994 | Taylor et al. | |
| 5,296,855 A * | 3/1994 | Matsuzaki et al. | 340/988 |
| 5,306,276 A | 4/1994 | Johnson et al. | |
| 5,320,625 A | 6/1994 | Bertin | |
| 5,325,029 A | 6/1994 | Janecke et al. | |
| 5,342,367 A | 8/1994 | Ferrante et al. | |
| 5,343,391 A | 8/1994 | Mushabac | |
| 5,358,526 A | 10/1994 | Tornier | |
| 5,376,093 A * | 12/1994 | Newman | 606/88 |
| 5,395,377 A | 3/1995 | Petersen et al. | |
| 5,417,694 A | 5/1995 | Marik et al. | |
| 5,423,827 A | 6/1995 | Mumme | |
| 5,431,653 A | 7/1995 | Callaway | |
| 5,468,244 A | 11/1995 | Attfield et al. | |
| 5,474,088 A * | 12/1995 | Zaharkin et al. | 600/595 |
| 5,486,177 A | 1/1996 | Mumme et al. | |
| 5,514,143 A | 5/1996 | Bonutti et al. | |
| 5,529,070 A | 6/1996 | Augustine et al. | |
| 5,540,696 A | 7/1996 | Booth, Jr. et al. | |
| 5,597,379 A | 1/1997 | Haines et al. | |
| 5,624,444 A | 4/1997 | Wixon et al. | |
| 5,628,750 A | 5/1997 | Whitlock et al. | |
| 5,681,316 A | 10/1997 | DeOrio et al. | |
| 5,688,282 A | 11/1997 | Baron et al. | |
| 5,720,752 A | 2/1998 | Elliott et al. | |
| 5,748,767 A | 5/1998 | Raab | |
| 5,769,861 A | 6/1998 | Vilsmeier | |
| 5,776,137 A | 7/1998 | Katz | |
| 5,916,219 A | 6/1999 | Matsuno et al. | |
| 6,036,696 A | 3/2000 | Lambrecht et al. | |
| 6,056,756 A | 5/2000 | Eng et al. | |
| 6,090,114 A | 7/2000 | Matsuno et al. | |
| 6,094,019 A * | 7/2000 | Saiki | 318/102 |
| 6,120,509 A | 9/2000 | Wheeler | |
| 6,122,538 A | 9/2000 | Sliwa, Jr. et al. | |
| 6,126,608 A | 10/2000 | Kemme et al. | |
| 6,162,191 A * | 12/2000 | Foxlin | 600/595 |
| 6,167,292 A | 12/2000 | Badano et al. | |
| 6,171,310 B1 | 1/2001 | Giordano | |
| 6,195,615 B1 * | 2/2001 | Lysen | 702/94 |
| 6,214,013 B1 | 4/2001 | Lambrech et al. | |
| 6,214,014 B1 | 4/2001 | McGann | |
| 6,246,898 B1 | 6/2001 | Vesely et al. | |
| 6,258,095 B1 | 7/2001 | Lombardo et al. | |
| 6,261,247 B1 | 7/2001 | Ishikawa et al. | |
| 6,348,058 B1 | 2/2002 | Melken et al. | |
| 6,354,011 B1 * | 3/2002 | Albrecht | 33/318 |
| 6,361,506 B1 | 3/2002 | Saenger et al. | |
| 6,381,485 B1 | 4/2002 | Hunter et al. | |
| 6,385,475 B1 | 5/2002 | Cinquin et al. | |
| 6,395,005 B1 | 5/2002 | Lovell | |
| 6,447,448 B1 | 9/2002 | Ishikawa et al. | |
| 6,470,207 B1 | 10/2002 | Simon et al. | |
| 6,471,637 B1 | 10/2002 | Green et al. | |
| 6,477,400 B1 | 11/2002 | Barrick | |
| 6,477,421 B1 | 11/2002 | Anderson et al. | |
| 6,478,799 B1 | 11/2002 | Williamson | |
| 6,499,488 B1 | 12/2002 | Hunter et al. | |
| 6,527,443 B1 | 3/2003 | Vilsmeier | |
| 6,551,325 B2 | 4/2003 | Neubauer et al. | |
| 6,595,997 B2 | 7/2003 | Axelson, Jr. et al. | |
| 6,607,487 B2 | 8/2003 | Chang et al. | |
| 6,640,128 B2 | 10/2003 | Vilsmeier et al. | |
| 6,679,916 B1 | 1/2004 | Frankle et al. | |
| 6,712,824 B2 | 3/2004 | Millard et al. | |
| 6,715,213 B2 * | 4/2004 | Richter | 33/328 |
| 6,743,235 B2 | 6/2004 | Rao | |
| 6,770,078 B2 | 8/2004 | Bonutti | |
| 6,827,723 B2 | 12/2004 | Carson | |
| 6,917,827 B2 | 7/2005 | Kienzle, III | |
| 6,923,817 B2 | 8/2005 | Carson et al. | |
| 6,928,742 B2 | 8/2005 | Broers et al. | |
| 6,947,783 B2 | 9/2005 | Immerz | |
| 7,007,699 B2 | 3/2006 | Martinelli et al. | |
| 7,021,140 B2 | 4/2006 | Perkins | |
| 7,048,741 B2 | 5/2006 | Swanson | |
| 7,094,241 B2 * | 8/2006 | Hodorek et al. | 606/87 |
| 7,194,295 B2 | 3/2007 | Vilsmeier | |
| 7,209,776 B2 | 4/2007 | Leitner | |
| 7,331,932 B2 | 2/2008 | Leitner | |
| 7,344,541 B2 | 3/2008 | Haines et al. | |
| 7,392,076 B2 | 6/2008 | Moctezuma de la Barrera | |
| 7,396,357 B2 | 7/2008 | Tornier et al. | |
| 7,497,029 B2 | 3/2009 | Plassky et al. | |
| 7,520,880 B2 | 4/2009 | Claypool et al. | |
| 7,547,307 B2 | 6/2009 | Carson et al. | |
| 7,559,931 B2 | 7/2009 | Stone | |
| 7,578,821 B2 | 8/2009 | Fisher et al. | |
| 7,611,520 B2 | 11/2009 | Broers et al. | |
| 7,621,920 B2 | 11/2009 | Claypool et al. | |
| 7,834,847 B2 | 11/2010 | Boillot et al. | |
| 2002/0077540 A1 | 6/2002 | Kienzle | |
| 2002/0133175 A1 | 9/2002 | Carson | |
| 2002/0198451 A1 | 12/2002 | Carson | |
| 2003/0019294 A1 | 1/2003 | Richter | |
| 2003/0105470 A1 | 6/2003 | White | |
| 2004/0243148 A1 * | 12/2004 | Wasielewski | 606/130 |
| 2005/0113846 A1 | 5/2005 | Carson | |
| 2005/0149040 A1 | 7/2005 | Haines et al. | |
| 2005/0222574 A1 | 10/2005 | Giordano et al. | |
| 2005/0251026 A1 | 11/2005 | Stone | |
| 2005/0251148 A1 | 11/2005 | Friedrich | |
| 2006/0142657 A1 | 6/2006 | Quaid et al. | |
| 2007/0162142 A1 | 7/2007 | Stone | |
| 2008/0183179 A1 | 7/2008 | Siebel et al. | |
| 2008/0249394 A1 | 10/2008 | Giori et al. | |
| 2008/0275451 A1 | 11/2008 | McAllister et al. | |
| 2009/0000626 A1 | 1/2009 | Quaid et al. | |
| 2009/0012532 A1 | 1/2009 | Quaid et al. | |
| 2009/0318836 A1 | 12/2009 | Stone et al. | |
| 2009/0318930 A1 | 12/2009 | Stone et al. | |
| 2009/0318931 A1 | 12/2009 | Stone et al. | |
| 2010/0016705 A1 | 1/2010 | Stone | |
| 2010/0063508 A1 | 3/2010 | Borja et al. | |
| 2010/0063509 A1 | 3/2010 | Borja et al. | |
| 2010/0064216 A1 | 3/2010 | Borja et al. | |
| 2010/0069911 A1 | 3/2010 | Borja et al. | |
| 2010/0076505 A1 | 3/2010 | Borja | |
| 2010/0100011 A1 | 4/2010 | Roche | |
| 2010/0100154 A1 | 4/2010 | Roche | |
| 2010/0137869 A1 | 6/2010 | Borja et al. | |
| 2010/0137871 A1 | 6/2010 | Borja | |
| 2010/0179605 A1 | 7/2010 | Branch et al. | |
| 2010/0182914 A1 | 7/2010 | DelRegno et al. | |
| 2010/0198275 A1 | 8/2010 | Chana et al. | |
| 2010/0204551 A1 | 8/2010 | Roche | |
| 2010/0204575 A1 | 8/2010 | Roche et al. | |
| 2010/0204955 A1 | 8/2010 | Roche et al. | |
| 2010/0249533 A1 | 9/2010 | Pierce et al. | |
| 2010/0249534 A1 | 9/2010 | Pierce et al. | |
| 2010/0249535 A1 | 9/2010 | Pierce et al. | |
| 2010/0249665 A1 | 9/2010 | Roche | |
| 2010/0249787 A1 | 9/2010 | Roche | |
| 2010/0249788 A1 | 9/2010 | Roche | |
| 2010/0249790 A1 | 9/2010 | Roche | |
| 2010/0249791 A1 | 9/2010 | Roche | |
| 2010/0250276 A1 | 9/2010 | Pierce et al. | |

| | | |
|---|---|---|
| 2010/0250284 A1 | 9/2010 | Roche et al. |
| 2010/0250571 A1 | 9/2010 | Pierce et al. |
| 2010/0326187 A1 | 12/2010 | Stein |
| 2010/0326194 A1 | 12/2010 | Stein et al. |
| 2010/0326210 A1 | 12/2010 | Stein et al. |
| 2010/0326211 A1 | 12/2010 | Stein |
| 2010/0327848 A1 | 12/2010 | Stein |
| 2010/0327880 A1 | 12/2010 | Stein |
| 2010/0328077 A1 | 12/2010 | Stein |
| 2010/0328098 A1 | 12/2010 | Stein et al. |
| 2010/0331633 A1 | 12/2010 | Stein |
| 2010/0331663 A1 | 12/2010 | Stein |
| 2010/0331679 A1 | 12/2010 | Stein |
| 2010/0331680 A1 | 12/2010 | Stein |
| 2010/0331681 A1 | 12/2010 | Stein et al. |
| 2010/0331682 A1 | 12/2010 | Stein et al. |
| 2010/0331683 A1 | 12/2010 | Stein et al. |
| 2010/0331685 A1 | 12/2010 | Stein et al. |
| 2010/0331687 A1 | 12/2010 | Stein et al. |
| 2010/0331704 A1 | 12/2010 | Stein et al. |
| 2010/0331718 A1 | 12/2010 | Stein |
| 2010/0331733 A1 | 12/2010 | Stein |
| 2010/0331734 A1 | 12/2010 | Stein |
| 2010/0331735 A1 | 12/2010 | Stein |
| 2010/0331736 A1 | 12/2010 | Stein |
| 2010/0331737 A1 | 12/2010 | Stein et al. |
| 2010/0331738 A1 | 12/2010 | Stein et al. |
| 2010/0331894 A1 | 12/2010 | Stein |
| 2010/0332152 A1 | 12/2010 | Stein |
| 2011/0032184 A1 | 2/2011 | Roche et al. |

FOREIGN PATENT DOCUMENTS

| | | |
|---|---|---|
| DE | 29704393 | 8/1997 |
| WO | WO 99/60939 | 12/1999 |
| WO | WO 02/17798 A1 | 3/2002 |
| WO | WO 2004/080323 | 9/2004 |
| WO | WO 2004/112610 | 12/2004 |
| WO | WO 2005/006993 | 1/2005 |
| WO | WO 2008/073999 A2 | 6/2008 |

OTHER PUBLICATIONS

The Academy of Orthopaedic Surgeons, *Academy News*, Mar. 1, 2001 (website: http://www.aaos.org/wordhtml/2001news/b6-01.htm.

Medical Research Ltd., *Clinical Goniometer*, 1997, pp. 1-2 (website: http://www.mie-uk.com/Gonio).

Biomet Orthopedics, Inc., *Universal Ringloc Acetabular Series* (website brochure).

Biomet Orthopedics, Inc., *Vision Acetabular Surgical Techniques* (website brochure).

DePuy, Johnson & Johnson, Co., *Summit Cemented Hip System*, undated (brochure).

510 (k) Summary for Total Knee Surgetics Navigation System, in 5 pages.

510 (k) Summary of Safety and Effectiveness for BrainLAB knee, in 5 pages.

Anderson MD., Kevin, et al., "Computer Assisted Navigation in Total Knee Arthroplasty", The Journal of Arthroplasty, 2005, vol. 20, No. 7, Suppl. 3, in 7 pages.

Arnold-Moore, et. al., Architecture of a Content Management Server for XML Document Applications, RMIT Multimedia Database Systems, Royal Melbourne Institute of Technology, Victoria Australia, in 12 pages.

Bargren, MD., et al, Alignment in Total Knee Arthroplasty, Correlated Biomechanical and Clinical Observations, Clinical Orthopaedics and Related Research, Mar. 1, 1983, Issue 173, pp. 178-183, Philadelphia.

Bathis, H. et al., "Alignment in total knee arthroplasty", The Journal of Bone & Joint Surgery (Br), 2004, 86-B, pp. 682-687, British Editorial.

Decking, MD., et al., Leg Axis After Computer-Navigated Total Knee Arthroplasty, The Journal of Arthroplasty, 2005, vol. 20, Issue 3, pp. 282-288.

Digioia III, MD., et al., "Comparison of a Mechanical Acetabular Alignment Guide with Computer Placement of the Socket", The Journal of Arthroplasty, Apr. 2002, vol. 17, No. 3, in 6 pages.

European Office Action for Application No. 04776379.2 , dated May 4, 2010, in 5 pages.

Goniometer, AllHeart.com, 2004, website: http://allheart.com/allheart, (1 page).

Hofstetter, Ph.D., et al., "Computer-Assisted Fluoroscopy-Based Reduction of Femoral Fractures and Antetorsion Correction", Computer Aided Surgery, 2000, vol. 5, pp. 311-325, Wiley-Liss, Inc.

Hsieh, Pang-Hsin, et al., "Image-guided periacetabular osteotomy: computer-assisted navigation compared with the conventional technique: A randomized study of 36 patients followed for 2 years", Acta Orthopaedica, Aug. 1, 2006, 77:4, pp. 591-597.

International Search Report for International Application No. PCT/US2009/051769 dated Nov. 19, 2009, in 3 pages.

Leenders, MD., et al., "Reduction in Variability of Acetabular Cup Abduction Using Computer Assisted Surgery: A Prospective and Randomized Study", Computer Aided Surgery, 2002, vol. 7, pp. 99-106.

Liebergall, Meir, et al., " Computerized Navigation for the Internal Fixation of Femoral Neck Fractures", The Journal of Bone & Joint Surgery Am, 2006, vol. 88, pp. 1748-1754.

Parratte, Sebastien, et al., "Validation and Usefulness of a Computer-Assisted Cup-Positioning System in Total Hip Arthroplasty. A Prospective, Randomized, Controlled Study", The Journal of Bone & Joint Surgery Am, 2007, vol. 89, pp. 494-499.

Ritter, M.D., et al., Postoperative Alignment of Total Knee Replacement, Its Effect on Survival, Clinical Orthopaedics and Related Research, Feb. 1, 1994, Issue 299, pp. 153-156, Philadelphia.

Sacks-Davis et. al., Atlas: A nested Relational Database System for Text Applications, IEEE Transations on Knowledge and Data Engineering, v.7, n. 3, Jun. 1995, pp. 454-470.

Schep, et al., "Computer assisted orthopaedic and trauma surgery State of the art and future perspectives", Injury Int. J. Care Injured 34, (website: www.elsevier.com/locate/injury), 2003 pp. 299-306.

Slomczykowski, et al., "Novel Computer-Assisted Fluoroscopy System for Intraoperative Guidance: Feasibility Study for Distal Locking of Femoral Nails", Journal of Orthopaedic Trauma, 2001, vol. 15, No. 2, pp. 122-131, Lippincott Williams & Wilkins, Inc., Philadelphia.

Written Opinion for International Application No. PCT/US2009/051769, dated Nov. 19, 2009, in 7 pages.

Zorman, David, et al., "Computer-assisted total knee arthroplasty: comparative results in a preliminary series of 72 cases", ActaOrthop. Belg., 2005, 71, pp. 696-702.

International Search Report for International Application No. PCT/US2011/022162, dated Jun. 16, 2011, in 4 pages.

Written Opinion for International Application No. PCT/US2011/022162, dated Jun. 16, 2011, in 9 pages.

International Preliminary Report for Application No. PCT/US2004/018244, dated Dec. 13, 2005, in 11 pages.

International Search Report for Application No. PCT/US2004/018244, dated Feb. 15, 2005, in 4 pages.

International Search Report for International Application No. PCT/US2009/051769 dated Nov. 11, 2009, in 11 pages.

Office Action for U.S. Appl. No. 11/182,528, dated Jun. 25, 2008, in 10 pages.

Office Action for U.S. Appl. No. 12/369,693, dated May 11, 2011, in 8 pages.

Office Action for U.S. Appl. No. 12/502,182, dated Oct. 8, 2010, in 13 pages.

Written Opinion of the ISR for Application No. PCT/US2004/018244, received Mar. 14, 2005, in 10 pages.

* cited by examiner

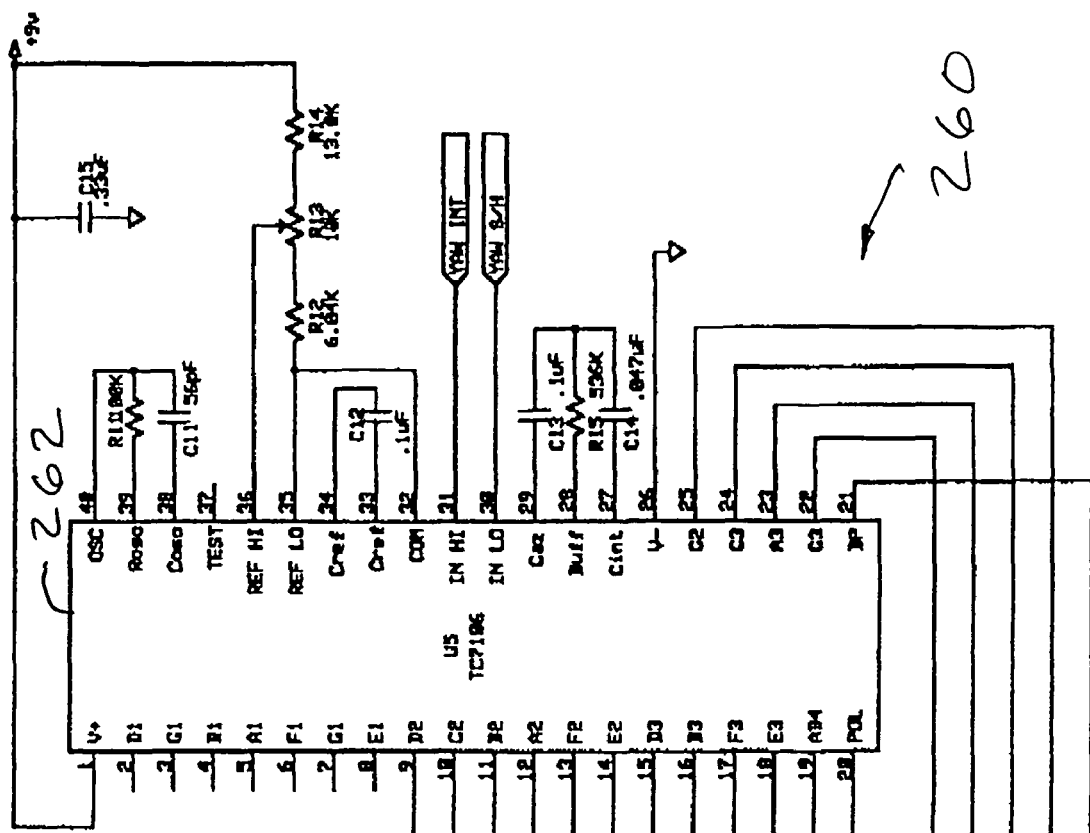
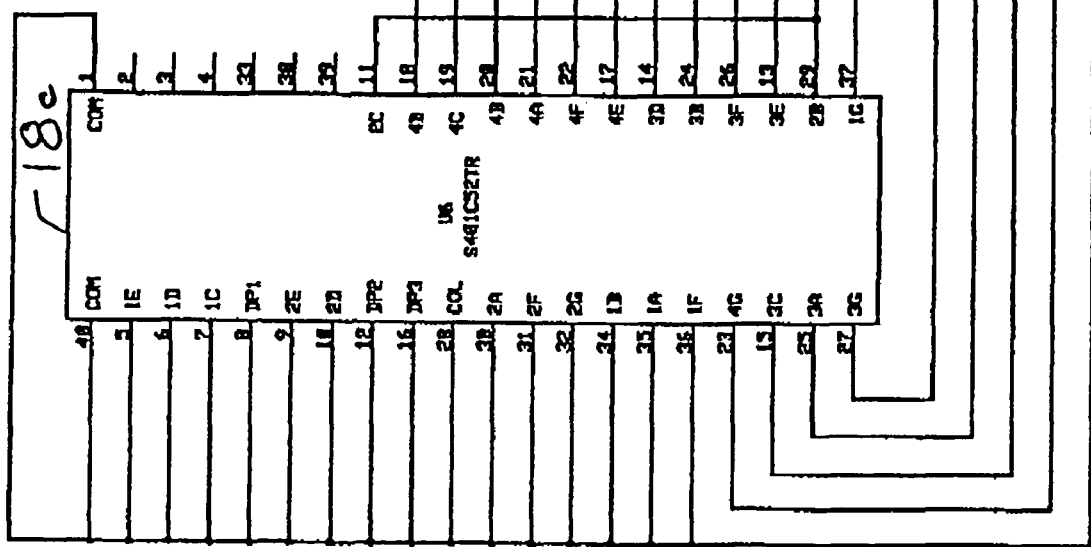
Fig. 12

SURGICAL ORIENTATION DEVICE AND METHOD

CROSS-REFERENCE TO RELATED APPLICATION(S)

This application claims the benefit of U.S. provisional application 60/476,998 filed Jun. 9, 2003, which is hereby incorporated by reference in its entirety.

TECHNICAL FIELD

The present invention relates to medical orientation and positioning devices and in particular to a device for orienting surgical instruments, implements, implants, prosthetics, and anatomical structures.

BACKGROUND

Correct positioning of surgical instruments and implants, used in a surgical procedure, with respect to the patient's anatomy is often an important factor in achieving a successful outcome. In certain orthopaedic implant procedures, such as totals hip replacement (THR) or arthroplasty, total knee arthroplasty (TKA), high tibial osteotomy (HTO), and total shoulder replacement (TSR), for example, the optimal orientation of the surgical implant enhances initial function and the long term operability of the implant. A misaligned acetabular prosthetic socket, for example, can lead to complications such as dislocation of the hip joint, decreased joint motion, joint pain, and hastened failure of the implant.

Obtaining satisfactory orientation and positioning of a prosthetic implant is often a challenging task for orthopaedic surgeons. Currently, one technique for orientation and positioning is accomplished using purely mechanical instruments and procedures based on anatomical landmarks. For example, the desired anteversion for an acetabular cup prosthesis within an acetabulum is accomplished by using external landmarks associated with a patient's pelvis. These methods, however, are subject to misalignment caused by variations in these external landmarks. These variations can be caused, for example, by failing to orient the patient's pelvis in the assumed neutral position on the operating table. Other orientation and positioning techniques involve sophisticated computer imaging systems, which are typically expensive and complicated to use.

There is a need in the art for an improved device and method for obtaining accurate orientation of surgical instruments and implants during various orthopaedic repair and replacement procedures. There is a further need for a device that is simple and easy to operate.

SUMMARY

The present invention, according to one embodiment is a surgical instrument for assisting a surgeon in obtaining correct orientation of an acetabular prosthetic socket in a patient's acetabulum. The instrument includes a support shaft adapted for supporting the acetabular prosthetic socket, a three-dimensional electronic orientation device securely coupled to the support shaft, and an acetabular alignment guide having at least three arms, the arms having a length sufficient to each contact a rim of the acetabulum.

According to another embodiment, the present invention is an apparatus for measuring and providing an indication of angular position with respect to a reference. The apparatus includes a rate sensor initially positioned with respect to a reference and operative to measure a rate of change of angular position with respect to the reference and provide a rate signal proportional to the rate of change of the angular position. It also includes an integrator selectively connected to the rate sensor and operative to integrate the rate signal and to provide an integral signal indicative of the relative angular position of the rate sensor. It further includes an averager selectively connected to the rate sensor and operative to average the rate signal and to provide an average signal indicative thereof. Finally, it includes a motion detector connected to the rate sensor and operative to switch the rate signal to (i) the averager when no motion is detected, and (ii) the integrator when motion is detected.

The present invention, in yet another embodiment, is a method of using an alignment instrument to align a prosthesis with an implant site. The method includes providing the instrument with a three dimensional measuring system capable of measuring angular position changes from a reference position, locating the instrument at a reference position with respect to the implant site using an alignment guide to contact the implant site, zeroing the measuring system while the alignment guide is in contact with the implant site and in the reference position, replacing the alignment guide with a prosthetic implant member, and positioning the instrument to a desired angular orientation with respect to the reference position using the measuring system to align the prosthesis with the implant site.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 12 is a detailed electrical schematic of an analog to digital converter and display for the YAW channel of the present invention.

Figure 1:
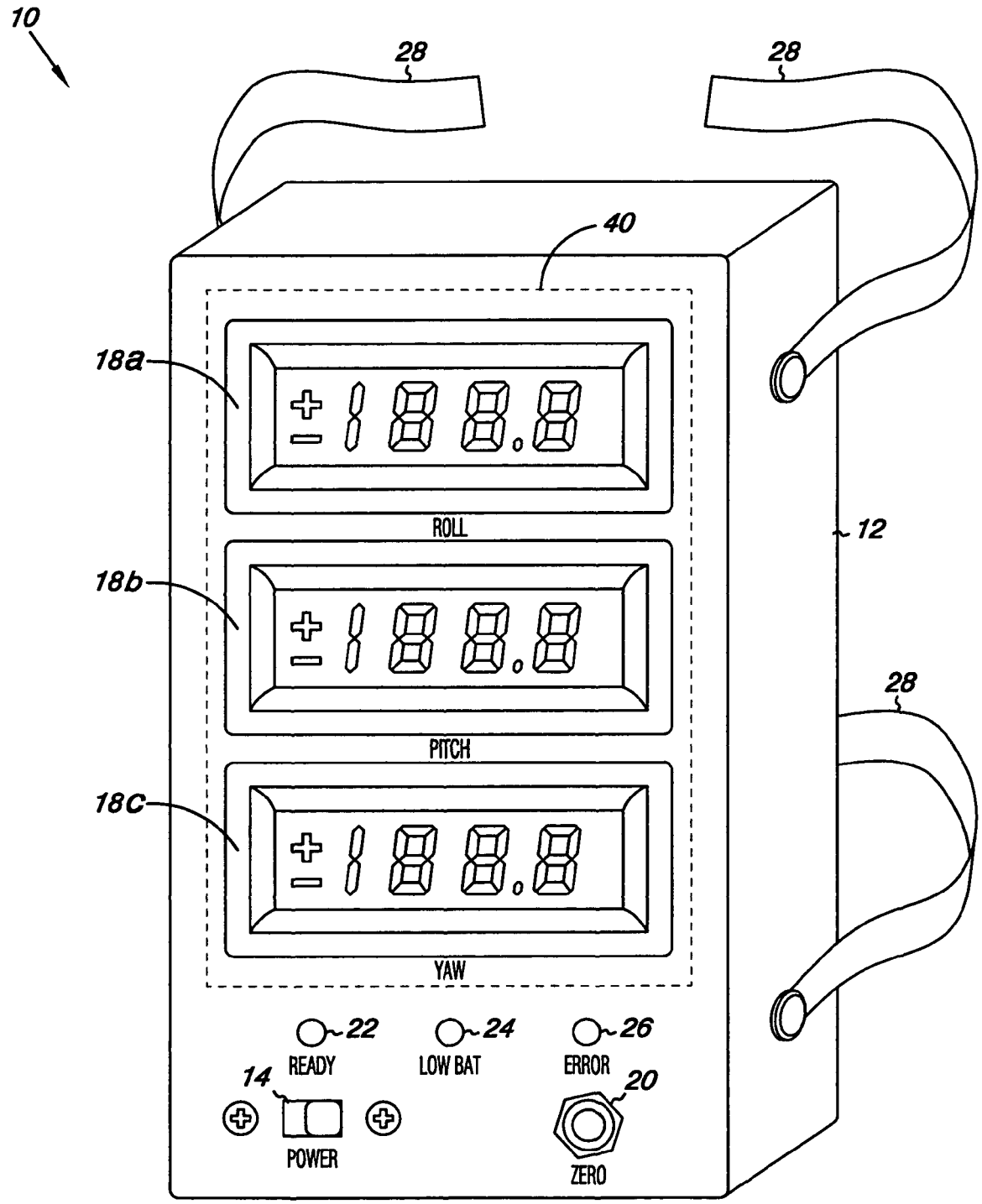
FIG. 1 is a perspective view of a surgical orientation device, according to one embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a perspective view of a surgical orientation device 10, according to one embodiment of the present invention. As shown in FIG. 1, the device 10 includes a housing 12, a power switch 14, displays 18, a zero button 20, and indicator lights 22, 24, and 26. The housing 12 contains the electronic circuitry and components necessary for device operation. The housing 12 may be made from any material suitable for use within a surgical field or patient treatment setting. The device 12 may be either disposable or reusable.

The displays 18, in the embodiment shown in FIG. 1, include a ROLL display 18a, a PITCH display 18b, and a YAW display 18c. These displays 18 provide an indication of the angular orientation of the device in three dimensions, which allow the device to function as a three-dimensional goniometer. The displays 18 may be a gauge of any type (e.g., analog meter, digital display, color bar, and thermocouple meter), and may be integrated on the housing or part of a separate, stand-alone device. The indicator lights include a wait/ready or RUN indicator 22, a LOW BATTERY indicator 24, and an overrange or ERROR indicator 26. In one exemplary embodiment, the indicator lights (e.g., LEDs) are integrated on the housing, to indicate when a positional property of interest, such as a angle, has been reached and/or not reached and/or exceeded.

In one embodiment, the device 10 further includes attachment straps 28 connected to the housing 12. The straps 28 are configured to allow attachment of the device 10 to a surgical instrument, implant, or prosthetic device. In one embodiment, the straps 28 are replaced with clips adapted for coupling with one or more surgical instruments. The device 10 may be transferable from instrument to instrument within an implant system or systems, or may be dedicated for use with one instrument. In one embodiment, further discussed below, the device 10 may in addition or in the alternative include sensors and displays for providing linear positioning information. Also, the device 10 may include only one or two of the ROLL, PITCH, and YAW displays 18 and the related circuitry.

In one embodiment, the device includes the sensors, further described below, for providing position and orientation signals. The sensor, for example, may be directly integrated into the body of the housing 12 or mounted onto the body of the housing 12. The sensors may be adhered to the housing 12, located inside the housing 12, or fabricated directly on the surface of the housing 12, for example, by depositing a layer of silicon on the housing 12 by chemical vapor deposition (CVD) or sputtering, and then building the devices in this silicon layer using techniques common to or derived from the art of semiconductor or MEMS processing.

In another embodiment, the device 10 is adapted to receive orientation and positioning signals from sensors located in an external device. The device 10 may have receptacles for attachment to such an external device through direct cable or wireless communication capabilities such as RF and IR. In that embodiment, such an external device is attached to the surgical instrument or prosthetic, and the device 10 is used by the surgeon as an interface. In one such embodiment, the sensor is connected, via wireless and/or wired connections, to a computer or other electronic instrument, which may record or display the sensor measurements (e.g., temperature), and which may at least partially control or evaluate the sensor. For example, an auxiliary computer or other electronic instrument may at least partially control the sensor by, for example, performing sensor calibration, performing real-time statistical analysis on the data from the sensor, or running error detection and correction algorithms on the data from the sensor.

In one embodiment, the device 10 includes communication capabilities for interacting with other equipment, for example, a computer generated image recreation system. It may, for example, be incorporated for use with computer aided surgical navigation systems, such as VectorVision available from BrainLab, Inc. of Germany, OrthoPilot, available from Aesculap, Inc. of Germany, HipNav, available from Casurgica, Inc., of Pittsburgh, Pa., and Navitrack, available from Orthosoft-Centerpulse Orthopedics, of Austin, Tex. In one such embodiment, data received from a sensor may be used by the computer system to control and/or modify a position of an implant. The computer or other electronic instrument may be configured to activate the appropriate controls or devices as necessary based on the data received from the sensor. Manual adjustments may also be made in response to the data received from the sensor. In another such embodiment, data from the sensor can be used in a feedback loop with positioning elements (either directly, via a computer or other electronic instrument, or by manual control) to maintain a desired property, such as an orientation or position.

Upon attachment of the device 10 to a surgical instrument, an operator, such as a surgeon for example, can use the device 10 to obtain three-dimensional orientation information. This combination of the device 10 with a surgical instrument is useful for assisting surgical procedures wherein one anatomical part is desirably aligned with another anatomical part. For example, when a limb-to-torso joint replacement is to be performed (e.g., THR or TSR), it is desirable to orient an implant (such as an acetabular cup) with the anatomical part within which it is to be implanted (such as the acetabulum) so that the implant will be properly positioned. For THR, the acetabular cup is desirably aligned with respect to the plane of the acetabulum. The present invention allows a surgeon to establish a reference plane corresponding to the plane of the acetabulum by positioning the device to physically align the device with the plane of the acetabulum and then zeroing the display when the device is aligned with the plane of the acetabulum to establish the reference plane. From then on, the device provides three dimensional angular information (ROLL, PITCH, and YAW) to the surgeon as the device is moved angularly with respect to the reference plane. FIGS. 2-13 show block diagrams and schematics illustrating the circuitry of the device 10. FIGS. 14-20 illustrate alignment guides used for identifying the desired reference plane, along with methods of using the present invention in joint replacement procedures.

Figure 2:
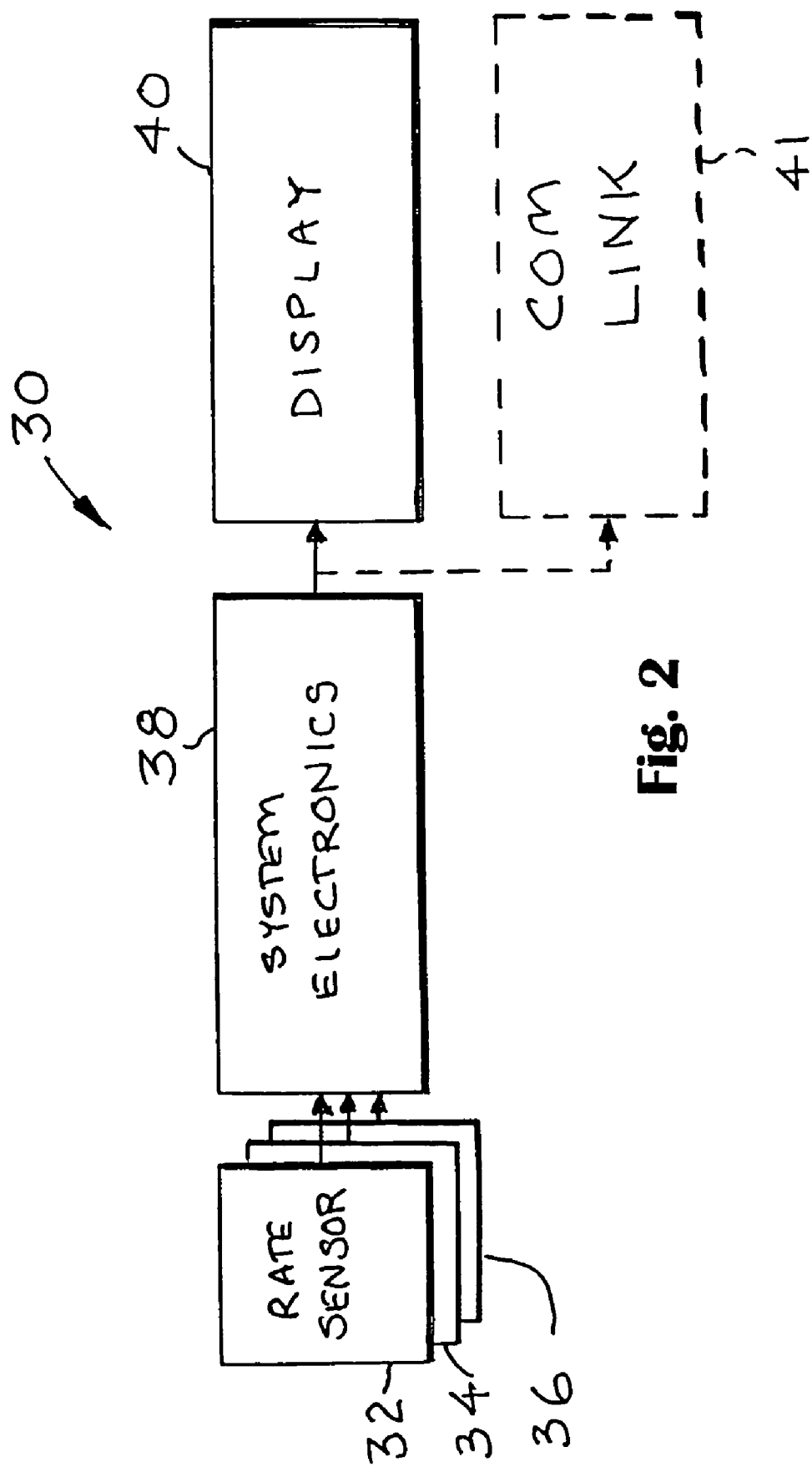
FIG. 2 is a simplified block diagram of the rate sensor, system electronics, and display useful in the practice of the present invention.

Referring to FIG. 2, position information is obtained using an angular measurement and display system 30, preferably having three RATE SENSOR blocks 32, 34, 36 which measure angular rate of change and deliver respectively, ROLL, PITCH, and YAW information to a SYSTEM ELECTRONICS block 38. The SYSTEM ELECTRONICS block converts the angular rate of change into angular position information and uses the DISPLAY block 40 to provide ROLL, PITCH, and YAW information in a human readable form, and additionally or alternatively, in electronic form for use by other systems, such as a data logger (not shown). An optional block 41 is shown in FIG. 2 to illustrate the communication capabilities mentioned above. Block 41 represents a communication link which may be as simple as a wire, or may include an interface which may be wired or wireless, and may encompass electrical, acoustical (preferably ultrasonic), radio frequency, or optical communication technologies, all of which are considered to be within the term "electronic," as that term is used herein. It is to be understood that block 41 represents an output with the angular orientation and (optionally) linear position information made available in a machine-readable (e.g., computer-compatible) format, while block 40 has a human readable display of the output information in a visually perceptable format.

Figure 3:
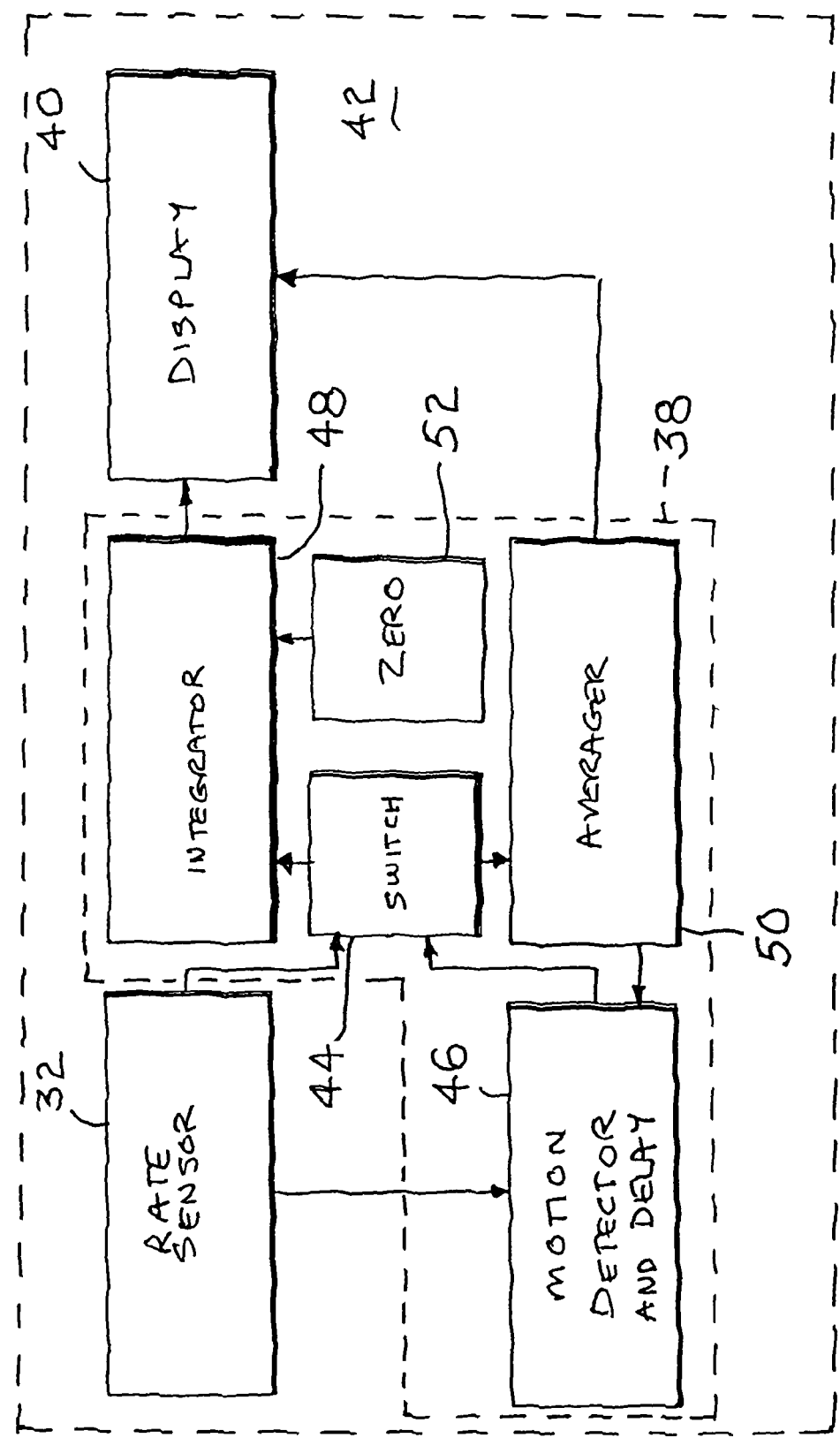
FIG. 3 is a more detailed block diagram of one channel of three corresponding to the block diagram of FIG. 2.

Referring now to FIG. 3, a more detailed block diagram of one channel, e.g., the ROLL channel 42, may be seen. It is to be understood that the other two (PITCH and YAW) channels are preferably identical to the ROLL channel 42. In FIG. 3, dashed line 38 encloses those blocks which form part of the SYSTEM ELECTRONICS 38 for the ROLL channel 42. Furthermore, it is to be understood that DISPLAY 40 in FIG. 3 refers to the display function for this channel, i.e., it includes a display of ROLL angular information.

For this channel, the RATE SENSOR 32 is preferably a MEMS (micro-electro-mechanical systems) device that provides angular rate of change information to a SWITCH block 44 and a MOTION DETECTOR AND DELAY block 46. SWITCH block 44 receives command information from the MOTION DETECTOR AND DELAY block 46 and directs the rate of change information to either an INTEGRATOR block 48 or an AVERAGER block 50. A ZERO block 52 permits resetting the INTEGRATOR 48 to a zero output in a manner to be described.

Figure 4:
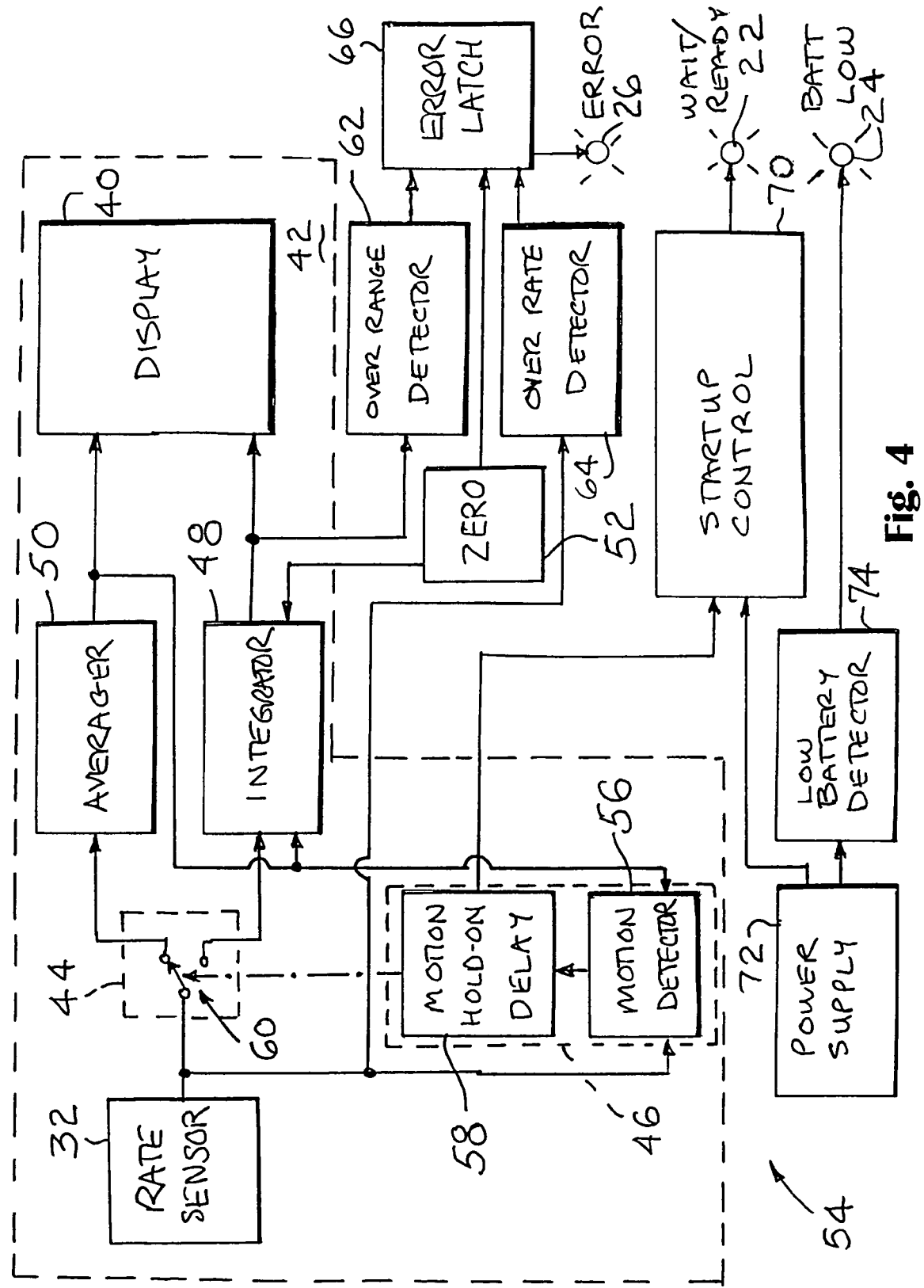
FIG. 4 is a still more detailed block diagram of one channel of the present invention, shown along with additional subsystems of the present invention.

Referring now also to FIG. 4, a more detailed block diagram 54 shows additional details of one channel (with the ROLL channel 42 used as an example) along with additional supporting functions of the SYSTEM ELECTRONICS 38. Each channel includes a MOTION DETECTOR block 56 and a MOTION HOLD-ON DELAY block 58 within the MOTION DETECTOR AND DELAY functional block 46 which controls the operation of a relay type switch 60 in SWITCH functional block 44 to switch between INTEGRATE and AVERAGE functions.

An OVERRANGE DETECTOR block 62 monitors whether the output of the INTEGRATOR block 48 reaches an OVERRANGE condition (corresponding to an angular position beyond which the system 30 is able to measure). An OVERRATE DETECTOR block 64 monitors the output of RATE SENSOR block 32 and provides an ERROR indication if the rate exceeds that which the system 30 is able to measure. Each of the blocks 62 and 64 are coupled to an ERROR LATCH block 66 which retains the ERROR condition (whether related to range or rate or both) until reset by the ZERO block 52. A STARTUP CONTROL block 70 monitors a POWER SUPPLY block 72 and the MOTION HOLD-ON DELAY block 58 and provides a WAIT/READY signal at a RUN indicator 22. A LOW BATTERY DETECTOR block 74 is connected to the POWER SUPPLY 72 and controls a LOW BATTERY indicator 24.

Figure 5:
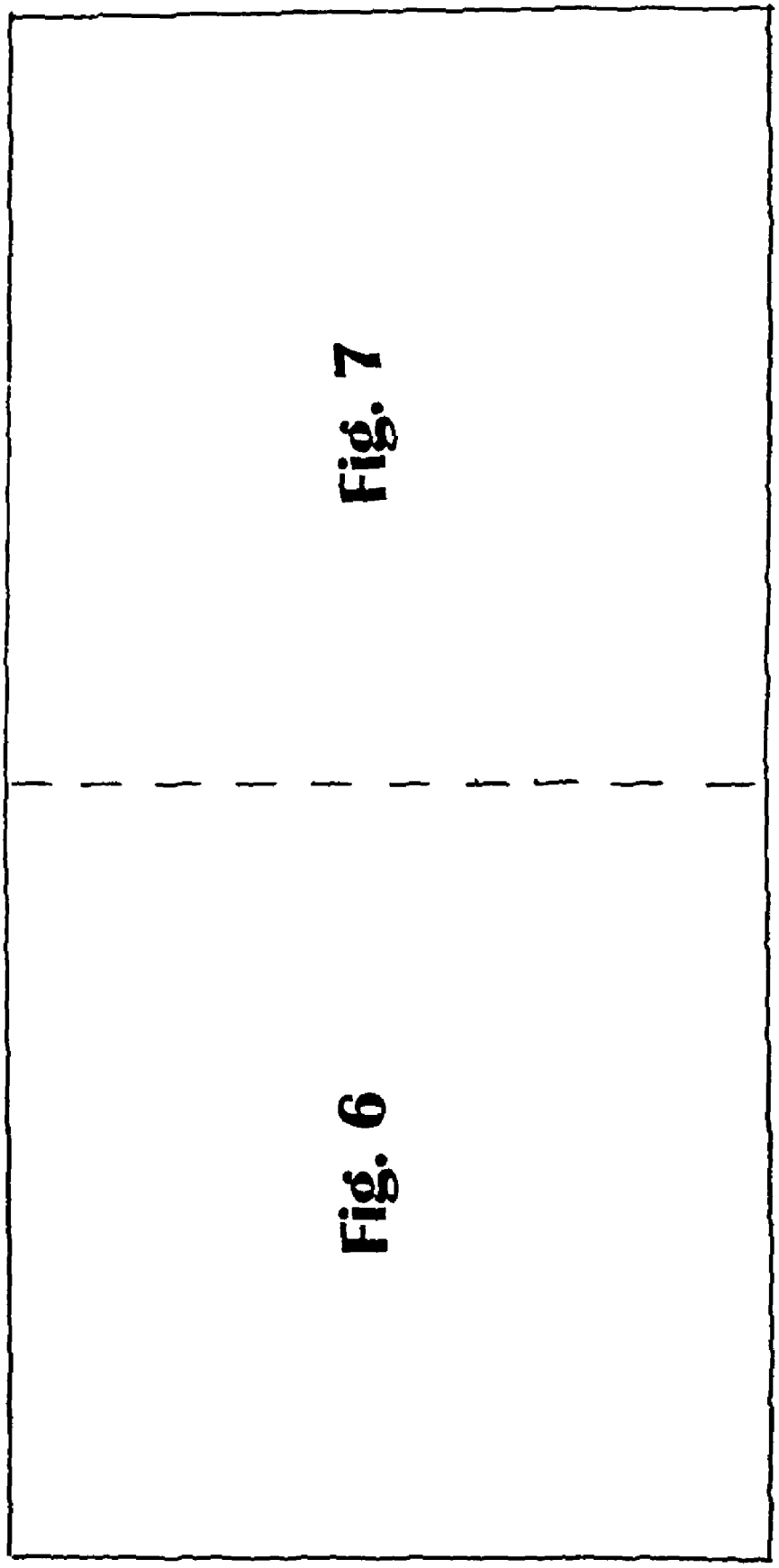
FIG. 5 is a key for FIGS. 6 and 7.
Figure 6:
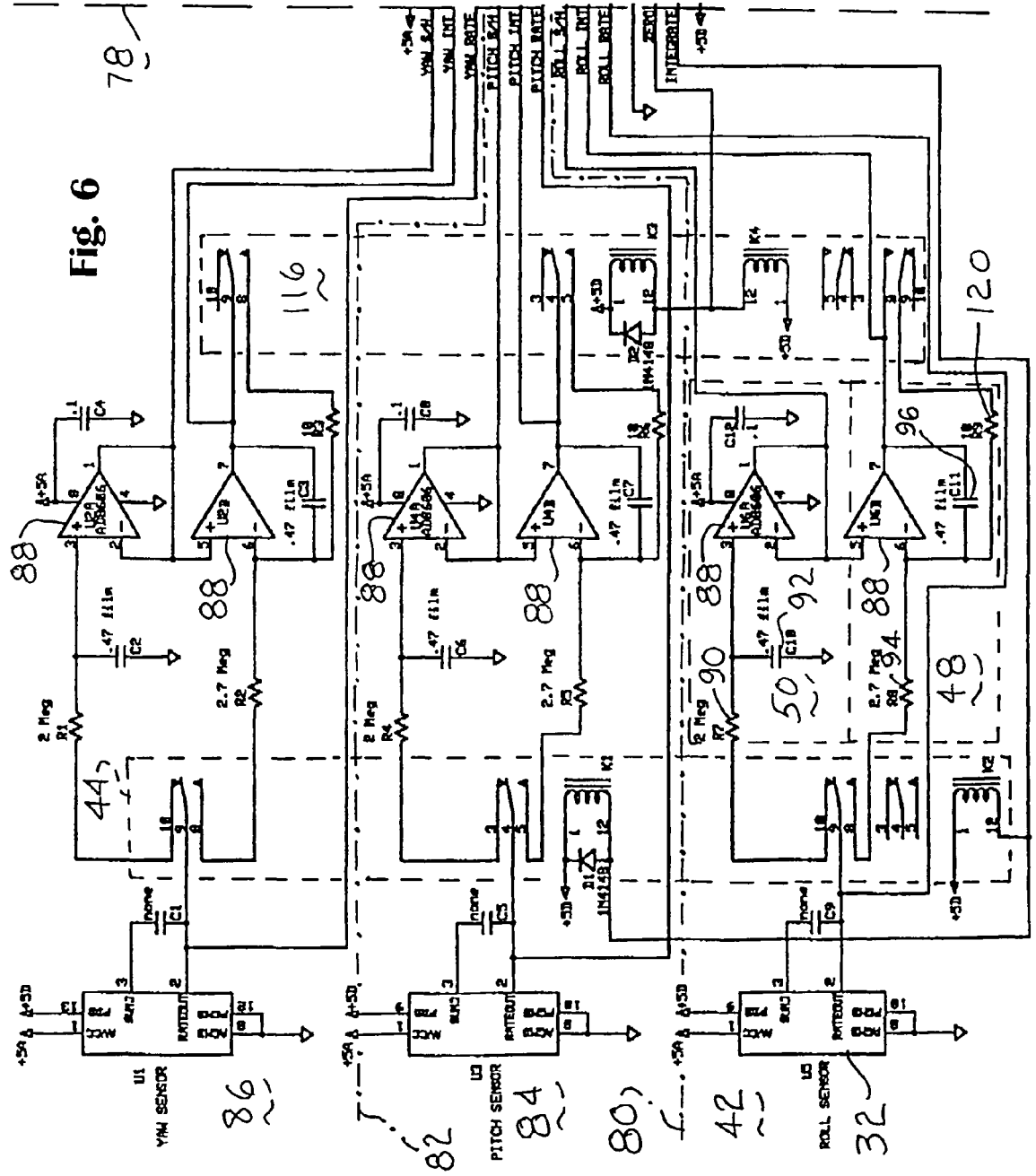
FIG. 6 is a detailed electrical schematic of ROLL, PITCH and YAW sensors and associated integrator and averager circuitry, useful in the practice of the present invention.
Figure 7:
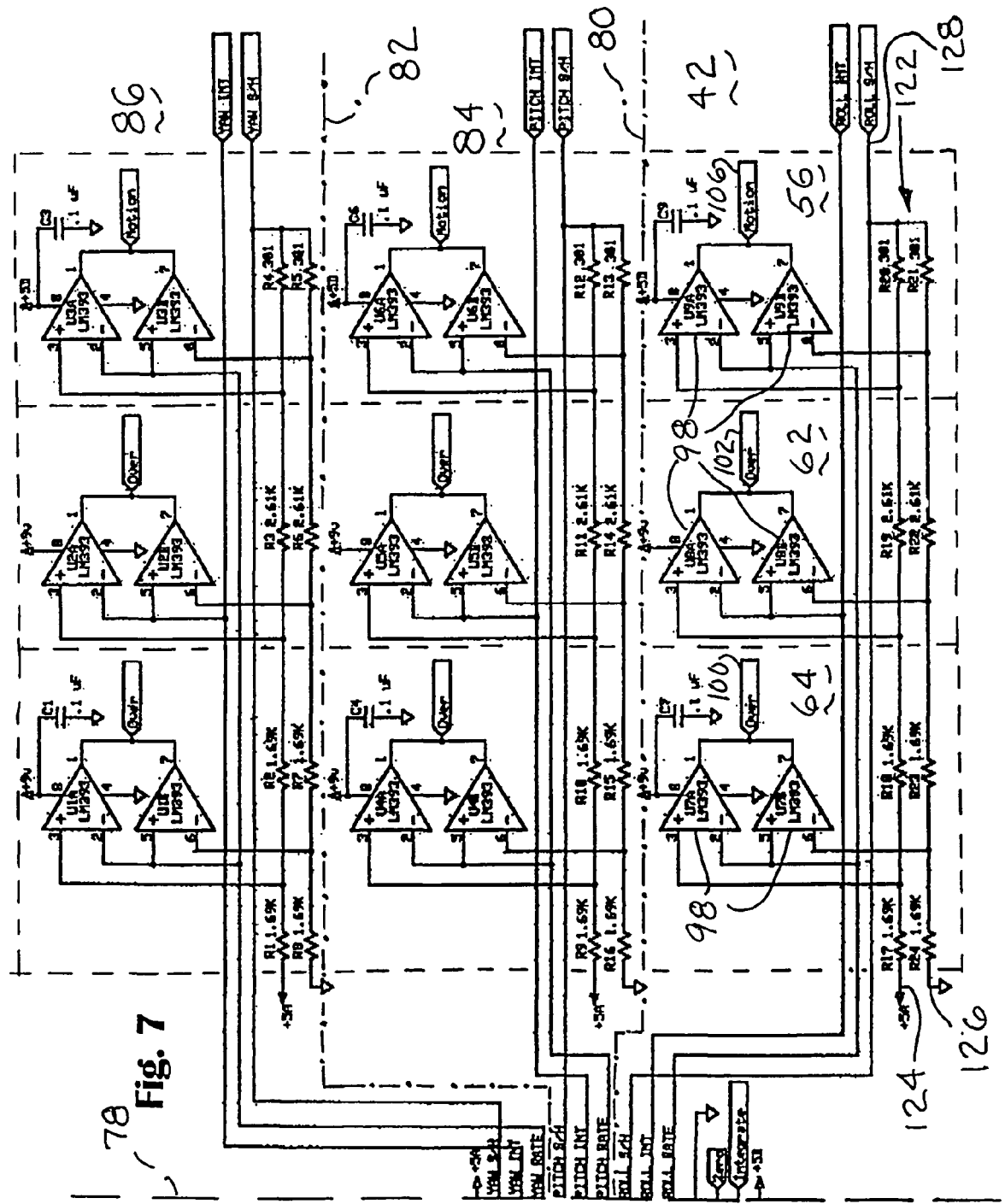
FIG. 7 is a detailed electrical schematic of overrange, overrate, and motion detectors and associated circuitry useful in the practice of the present invention.

Referring now to FIGS. 5, 6, and 7, FIG. 5 is a key to the electrical circuit schematics shown in FIGS. 6 and 7, which are to be understood to be joined at line 78. Dot dash line 80 separates the ROLL channel 42 from a PITCH channel 84. Dot dash line 82 separates the PITCH channel 84 from a YAW channel 86. Since the components and interconnections are the same for each of channels 42, 84, and 86, only ROLL channel 42 will be described, it being understood that the same description applies to each of the other channels, as well.

ROLL sensor 32 (and the PITCH and YAW sensors) are each preferably an ADXRS150 150 degree/second angular rate sensor (gyroscope) on a single chip, in a MEMS technology, available from Analog Devices, One Technology Way, P.O. Box 9106, Norwood, Mass. 02062-9106. It is to be understood that the ROLL, PITCH, and YAW sensors are mounted in a conventional orthogonal 3-dimensional (x-y-z) orientation. Each sensor produces an output voltage RATE-OUT that is proportional to the angular rate of rotation of that respective sensor. The output voltage is nominally 2.5 volts for zero rotation. The zero rotation output (or NULL) voltage varies from device to device, and with time and with temperature. The RATEOUT voltage varies above and below NULL for positive and negative rotational movement, respectively. The RATEOUT scale factor is typically 12.5 millivolts per degree per second with a full scale corresponding to 150 degrees per second. The ROLL sensor RATEOUT signal is also identified as a ROLL RATE signal. It is to be understood that each sensor responds in one plane only, and hence three separate sensors are mounted orthogonally to each other to achieve response in all three conventional mutually perpendicular (x, y, and z) axes.

The variation in sensor NULL voltage and the requirement to accurately process small rates of rotation make it desirable to establish an automatically self adjusting NULL reference. When the system is not physically rotating about any of the three x, y, z axes, the RATEOUT signal is connected through SWITCH block 44 to a low pass filter to produce an averaged representation of the RATEOUT voltage. This is the NULL voltage and it adjusts over time to sensor variations. When angular motion is detected in one or more of the three x, y, z axes, the SWITCH block (in response to an INTEGRATE signal [on line 140] from block 58, see FIG. 8) the RATEOUT signal is switched from the AVERAGER 50 to the INTEGRATOR 48.

At this time, since the input to the AVERAGER 50 is open circuited, the AVERAGER circuit 50 then enters a "hold" mode and retains the most recent previous NULL voltage, using that NULL voltage as a reference throughout the duration of the motion. The ROLL channel 42 NULL voltage is buffered by an operational amplifier 88 and delivered as a ROLL S/H signal. The operational amplifier integrated circuits 88 in the INTEGRATOR and AVERAGER circuits 48 and 50 are preferably AD8606 type op amps, available from Analog Devices. AVERAGER circuit 50 uses a low pass filter made up of a 2 MEG ohm resistor 90 and a 0.47 microfarad capacitor 92, resulting in a time constant of one second, which has been found to work well. However, it is to be understood that other part values and other time constants may be used, while still remaining within the scope of the present invention. The capacitor 92 preferably has a low leakage and low dissipation factor.

Angular position is the time integral of rotation rate. When motion is detected, the SWITCH block transfers the RATEOUT signal to the INTEGRATOR circuit 48 to compute angular position. The output of the ROLL INTEGRATOR 48 is available as a ROLL INT signal. INTEGRATOR circuit 48 uses a 2.7 MEG ohm resistor 94 and a 0.47 microfarad capacitor 96 to perform the integration. The reference for the integration is the no-motion NULL voltage for that channel. The capacitor 96 preferably has low leakage and a low dissipation factor. The integrating resistor 94 in conjunction with capacitor 96 provides a full scale range of over +120 degrees.

The INTEGRATOR 48 is reset to zero by discharging the capacitor 96. When the ZERO button 20 is depressed, relay 116 is energized by the ZERO signal on terminal 118 (see FIG. 8). The relay 116 discharges capacitor 96 through a 10 ohm resistor 120 to limit the discharge current.

Referring now most particularly to FIG. 7, in ROLL channel 42, integrated circuit comparators 98 are preferably LM393 type low power, low offset voltage comparators, available from National Semiconductor Corporation, 2900 Semiconductor Drive, P.O. Box 58090, Santa Clara, Calif., 95052-8090. If the sensor 32 is rotated too fast, the sensor output will saturate and the display would be incorrect. Similarly if the sensor is rotated through too great an angle, the integrator will saturate and the display would be incorrect. OVERRATE and OVERRANGE detectors 64 and 62 are provided to warn the operator in the event of the occurrence of either or both of these errors. There are three OVERRATE detectors and three OVERRANGE detectors, one pair for each of axes x, y, z, corresponding to ROLL, PITCH, and YAW channels 42, 84, and 86. Each channel has a window comparator circuit for each of the OVERRANGE and OVERRATE detectors. The comparators 98 in the OVERRATE circuit 64 provide the OVERRATE signal on a terminal 100, and the comparators 98 in the OVERRANGE circuit 62 provide the OVERRANGE signal on a terminal 102. Comparators 98 in circuit 64 monitor and compare the ROLL RATEOUT signal to a fixed level, and comparators 98 in circuit 62 compare the output of the ROLL INTEGRATOR circuit 48 to a fixed level. When the RATEOUT signal exceeds a predetermined level, either positive or negative, the window comparator made up of comparators 98 in the OVERRATE circuit 64 determines that the system is in an OVERRATE error condition. The threshold is set to approximately 150 degrees per second by a tap on the voltage divider string 122.

The output of the ROLL INTEGRATOR circuit 48 is sent to another window comparator made up of integrated circuit comparators 98 in the ROLL portion or channel of OVERRANGE circuit 62. When the INTEGRATOR circuit output (ROLL INT) exceeds a predetermined threshold, the ROLL channel portion of circuit 62 determines that the system is in an OVERRANGE error condition. The threshold is set at approximately 120 degrees by a tap on the voltage divider string 122. The twelve comparators in circuits 62 and 64 have open collector outputs. The six OVERRATE outputs (including the ROLL OVERATE output at terminal 100) together with the six OVERRANGE outputs (including the ROLL OVERRANGE output at terminal 102) are connected together. Both terminals 100 and 102 (i.e., all twelve comparator outputs) are connected to terminal 104 in the ERROR LATCH circuit 66 (see FIG. 8) and form the OVER signal. The OVER signal goes LOW whenever any one of the twelve comparators senses an error condition. Terminal 104 receives the OVER signal as an active LOW signal setting a type 74HC74 D type flip flop 150, available from Fairchild Semiconductor Corporation, 82 Running Hill Road, South Portland, Me. 04106. The flip-flop 150 is configured as a SET-RESET memory element. The "Q" output drives the ERROR indicator 26, which is preferably a red LED. The flip-flop 150 is reset by the ZERO signal on terminal 118.

Comparators 98 in the MOTION DETECTOR circuit 56 compare the output of the ROLL rate sensor 32 to a fixed level and provide a MOTION signal representative of whether the ROLL rate sensor 32 has experienced motion or not. When rotational motion is detected, the RATEOUT signal deviates from the NULL or no-motion voltage. The RATEOUT signal is sent to a "window" comparator made up of comparators 98 in the MOTION DETECTOR circuit 56. When the RATEOUT signal deviates from the NULL voltage by a predetermined amount or threshold (either positive or negative) the window comparator detects rotational motion. A threshold of one degree per second has been found to be preferable, but it is to be understood to be within the scope of the present invention to use other values, in the alternative.

Figure 8:
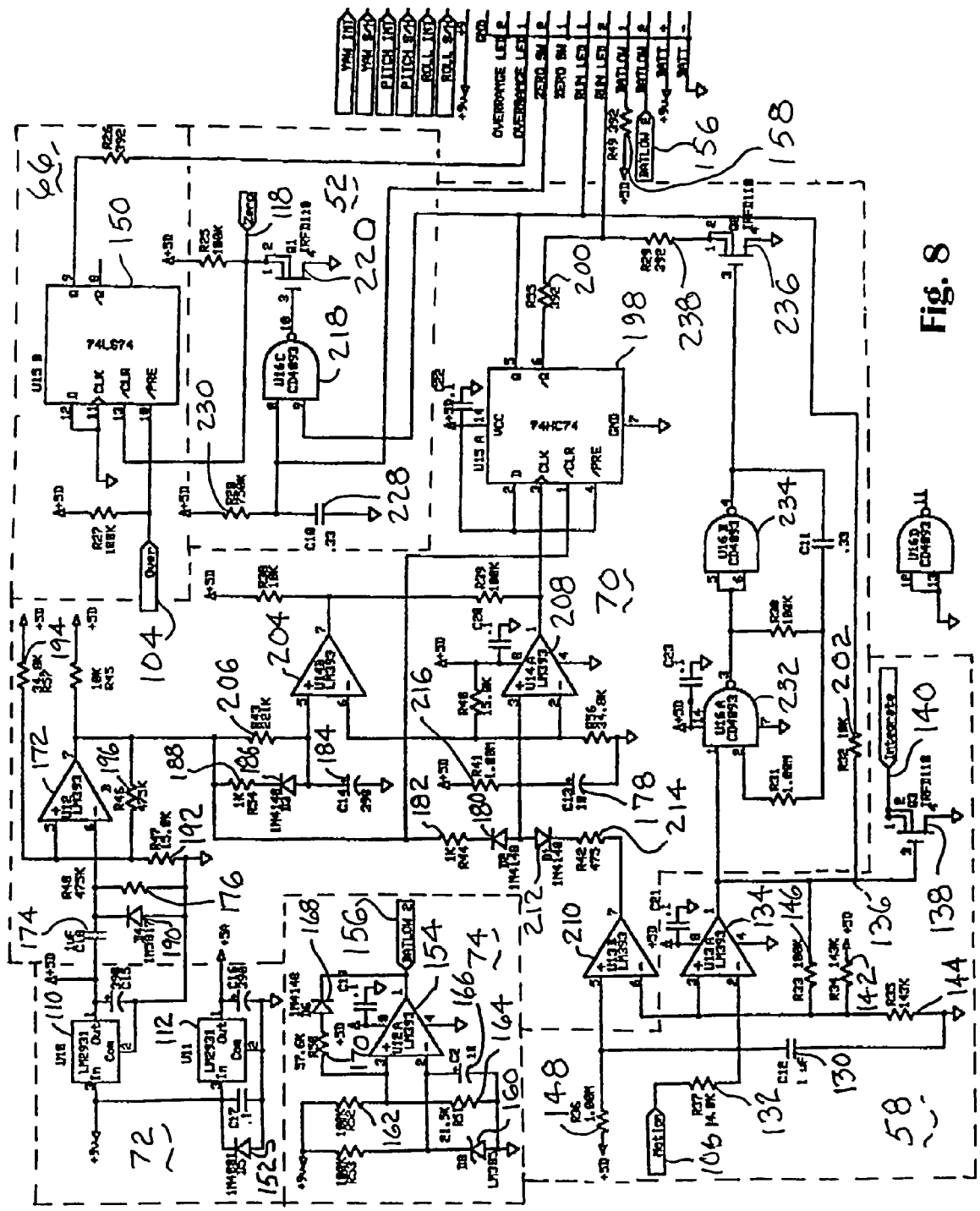
FIG. 8 is a detailed electrical schematic of the additional subsystems of FIG. 2.

A tap on a voltage divider string 122 sets the ROLL comparator MOTION thresholds. The divider 122 is connected between +5A 124 and circuit common 126, with the center point connected to the NULL voltage (ROLL S/H) line 128. This provides that the thresholds are referenced to the NULL voltage and compensates for drift and device-to-device variations in the NULL voltage. The MOTION signal appears on terminal 106 in MOTION DETECTOR circuit 56 and is connected to corresponding MOTION terminal 106 in the MOTION HOLD-ON DELAY circuit 58 (see FIG. 8). Each of circuits 56, 62, and 64 are provided with a pair of comparators 98 in the ROLL channel 42 so as to provide a bipolar (±) comparator function. All six MOTION comparators (including ROLL channel comparators 98) in channels 42, 84 and 86 have open collector outputs which are connected together via MOTION terminal or line 106. It is to be understood that the signal on MOTION line 106 will go to a LOW state whenever any one of the six comparators senses motion. Referring now also to FIG. 8, and more particularly, to circuit 58, when the MOTION signal on terminal 106 goes LOW, a 1 microfarad capacitor 130 will discharge through a 14.8K ohm resistor 132 causing a comparator 134 to deliver a HIGH output on line 136. This turns on an IRFD 110 type FET transistor 138 which pulls the INTEGRATE line 140 LOW.

The IRFD 110 type FET transistor is available from International Rectifier at 233 Kansas St. El Segundo, Calif. 90245 USA Comparator 134 is preferably a type LM393. When the INTEGRATE line 140 goes LOW, the relay 60 in SWITCH block 44 transfers the system from "average" mode to "integrate" mode. A pair of 143 K ohm resistors 142 and 144 set the threshold voltage for comparator 134 and a 100 K ohm resistor 146 provides hysteresis.

When the angular movement stops, the RATEOUT signal returns to the NULL voltage. The window comparators return to the open-collector state, allowing the capacitor 130 to slowly charge through a 1 MEG ohm resistor 148. The system 30 remains in the "integrate" mode until capacitor 130 charges sufficiently to switch comparator 134, which is approximately 0.7 seconds. This allows the system 30 to register any small movements the operator may make at the end of a gross movement. Such small movements may not otherwise be enough to activate the MOTION DETECTOR circuit 56.

After the 0.7 second delay, comparator 134 switches and the INTEGRATE line goes HIGH, terminating the "integrate" mode. At this point the relay 60 releases and the mechanical shock of the release is sensed by at least one of the sensors causing a noise output on one or more RATEOUT lines. This noise output can be large enough to retrigger the MOTION DETECTOR circuit 56, resulting in continuous cycling of relay 60. Such undesirable cycling is prevented by resistor 132 delaying discharge of capacitor 130 until the transient noise caused by the relay release has passed. Alternatively, relay 60 may be shock mounted.

Referring now again to FIG. 8, the STARTUP CONTROL circuit 70, POWER SUPPLY circuit 72, and LOW BATTERY DETECTOR circuit 74 may be seen. The STARTUP CONTROL circuit 70 has four functions. It generates a master reset pulse to initialize the system at power on. It provides a three minute warm-up period for the sensors. It enforces the requirement that the sensors not be moving for 10 seconds at the end of the warm-up period (to set the "no-motion" reference). It also gives the user feedback about the system status via the WAIT/READY status of the RUN indicator 22.

An LM 393 type comparator 172 generates a master reset pulse. The pulse is active LOW, with a pulse width of approximately 0.6 seconds, determined by a 1 microfarad capacitor 174 and a 475K ohm resistor 176. The pulse width is selected to be long enough to fully discharge a 10 microfarad capacitor 178 (through a diode 180 and a 1K ohm resistor 182) and at least partially discharge a 390 microfarad capacitor 184 (through a diode 186 and a 1K ohm resistor 188). The discharge of capacitors 178 and 184 is necessary to handle the situation where the system 30 is turned OFF and then immediately turned ON again. A 1N5817 type diode 190 protects comparator 172 and quickly discharges capacitor 174 on power down. A 15.0K ohm resistor 192 and a 34.8K ohm resistor 194 provide the reference voltage for comparator 172, and a 475K ohm resistor 196 provides hysteresis.

The master reset pulse also clears a WAIT/READY flip flop 198, which is preferably a 74HC74 type D flip flop. Flip flop 198 is cleared during the warm-up or WAIT period and is SET when the system 30 enters the READY state. Flip flop 198 drives the RUN indicator 22, which is preferably a yellow/green two color LED driven differentially by the Q and Q-not outputs at pins 5 and 6 of the device 198. Indicator 22 is preferably illuminated YELLOW during the WAIT or warm-up period, and switches to a GREEN illumination when the system enters the READY mode. A 392 ohm resistor 200 provides current limiting for the RUN indicator 22.

A 10K ohm resistor 202 connected to the Q output (pin 5) of flip flop 198 provides an input to the FET transistor 138 which serves as a relay driver for relay 60. When the system is in the WAIT mode or warm-up period, the input provided through resistor 202 forces the system to the AVERAGE mode by connecting the sensors to the AVERAGER amplifiers, since the Q output remains LOW during the warm-up period.

An LM 393 comparator 204 is the warm-up timer. A 221K ohm resistor 206 and capacitor 184 set the duration of the warm-up period. At the end of the warm-up period, the output (at pin 7) of comparator 204 goes to an open collector condition. This clocks the WAIT/READY flip flop 198 into the READY state, provided that 10 seconds have elapsed with no motion at the end of the warm-up period.

The 10 second "no-motion" requirement is enforced by a 10 second timer, which uses an LM 393 type comparator 208. The 10 second timer monitors the MOTION signal on line 106 (buffered through another LM 393 type comparator 210). If any of the sensors detect motion, capacitor 178 will be held discharged by comparator 210 acting through a diode 212 and a 475 ohm resistor 214. When none of the sensors detect motion, capacitor 178 will begin to charge through a 1.00 MEG ohm resistor 216. If no motion is detected for 10 seconds, the output (at pin 1) of comparator 208 will go to an OPEN condition, releasing the CLOCK input (at pin 3) of flip flop 198. The result is that the WAIT/READY flip flop is SET only after both the warm-up period has elapsed, and the system 30 has not detected motion for 10 seconds.

The POWER SUPPLY circuit 72 utilizes two integrated circuit voltage regulators 110 preferably LM2931 type, available from National Semiconductor Corporation. Regulators 110 and 112 each provide regulated +5 volts DC power to the various circuits shown. Regulator 110 provides power to digital circuits in system 30 (indicated by "+5D") and regulator 112 provides power to the analog circuits (particularly amplifiers 88, as indicated by "+5A). The sensors, (including ROLL sensor 32) require both analog and digital power. Separate analog and digital circuit common paths or "ground" traces are used to segregate analog and digital power supply currents, with the exception that only the analog ground is taken to the printed circuit board(s) (not shown) on which the sensors are mounted, because the digital currents are low in the sensors. A 9 volt battery 272 (see FIG. 9) provides power to the regulators 110, 112 and also to various other components and subcircuits, such as comparators 98 and A/D converter 114 (shown in FIG. 10). A diode 152 protects against reverse battery polarity.

An LM393 type comparator 154 is used for the LOW BATTERY DETECTOR 74. When the battery voltage drops below approximately 6.8 volts, comparator 154 switches, driving the signal on the BATLOW 2 terminal 156 LOW, turning on the BATTERY LOW indicator 24, which is preferably a red LED. The LED is supplied through a 392 ohm resistor 158. A precision voltage reference diode 160 sets a reference voltage at the "−" input (pin 2) of comparator 154 to 1.2 volts. A 100K ohm resistor 162 and a 21.5K ohm resistor 164 set the voltage at the "+" input (pin 3) of comparator 154 to 1.2 volts when the battery voltage is 6.8 volts. A 10 microfarad capacitor 166 delays the rise of the reference voltage at pin 2 of comparator 154 to force the comparator output voltage at the BATLOW 2 terminal 156 HIGH at power on. A diode 168 and a 57.6K ohm resistor 170 provide hysteresis to lock the output 156 in a LOW state once a low battery condition is detected. This prevents the BATTERY LOW indicator 24 from cycling ON and OFF in response to changing current demands on the battery 272, causing the battery voltage to fluctuate above and below 6.8 volts.

FIG. 8 also includes the details of the ZERO block or circuit 52. A CD4093 type NAND Schmitt Trigger integrated circuit has a NAND gate 218 driving an IRFD 110 type FET transistor 220 which energizes relay 116 for the ZERO function (see FIG. 6). One input (at pin 9) of NAND gate 218 is connected to the Q output (at pin 5) of the WAIT/READY flip flop 198. This holds the system 30 in the ZERO state or condition during the warm-up period. When the system enters the READY mode, the ZERO condition is cleared and the INTEGRATOR circuit 48 is enabled. Manual ZERO is accomplished by closing a ZERO switch 224 (see FIG. 9) which is connected between circuit common ("GND") and an input at pin 8 on NAND gate 218. Pushing the ZERO button closes switch 224, connecting the pin 8 input of NAND gate 218 to circuit common, at which time NAND gate 218 turns on transistor 220. When the switch 224 is released, it opens, allowing a 0.33 microfarad capacitor 228 to charge through a 750K ohm resistor 230, producing a ZERO pulse of at least 250 milliseconds.

When the system 30 detects motion, the user is given visual feedback by flickering the RUN indicator 22 with GREEN illumination. NAND gates 232 and 234 (also type CD4093) form a square wave oscillator with a period of about 50 milliseconds. When motion is detected, the oscillator is enabled by comparator 134 releasing the input at pin 1 of gate 232 to go HIGH. The oscillator output (at pin 4 of gate 234) drives an IRFD 110 type FET transistor 236. When transistor 236 is ON, it increases the current in the RUN indicator LED 22 by providing a path to circuit common through a 392 ohm resistor 238. The transistor 236 is turned ON and OFF every 50 milliseconds while the system senses motion, providing a visually perceptible feedback or indication to the user that the system 30 is sensing motion.

Figure 9:
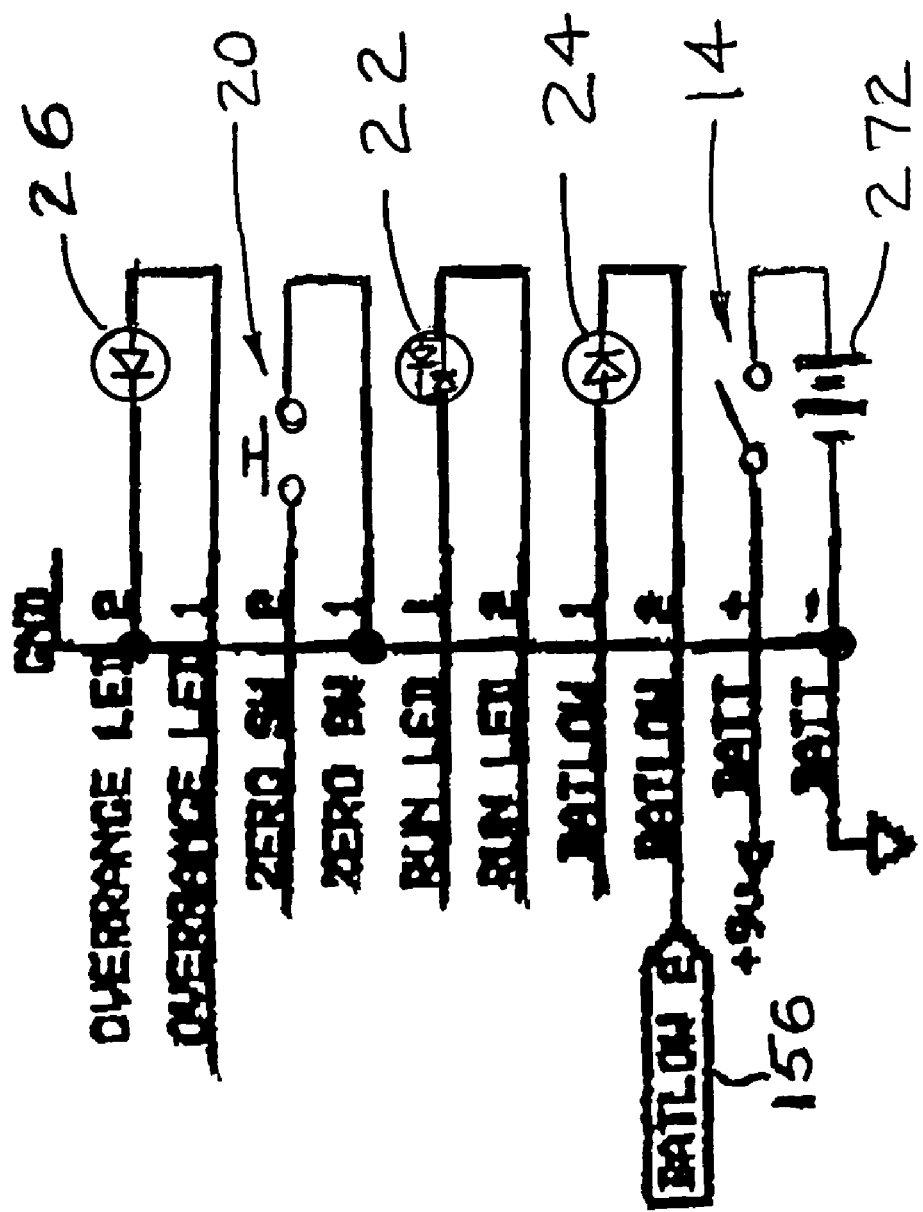
FIG. 9 is a wiring diagram for certain parts of the present invention.

Referring now to FIG. 9, a wiring diagram for connection of various parts to the STARTUP CONTROL 70 and ZERO block 52 of system 30 may be seen. It is to be understood that the the connections shown correspond to the lowermost connections on the right hand side of FIG. 8. A power switch 14 may be used to provide ON-OFF control of the system 30. Battery 272 is preferably a 9 volt battery. The ZERO switch 224 is preferably a normally OFF, momentary ON, spring return pushbutton type switch.

Figure 10:
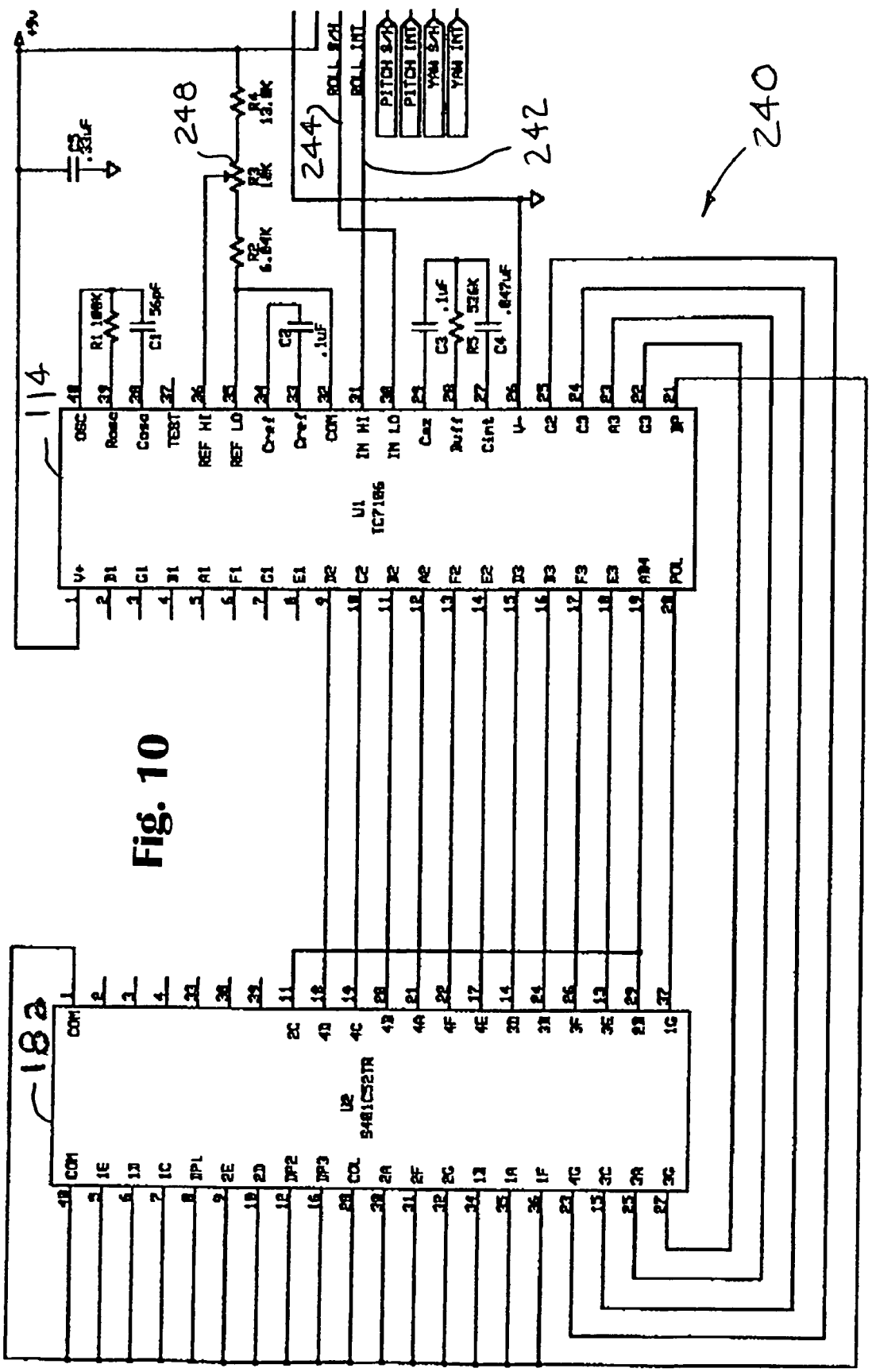
FIG. 10 is a detailed electrical schematic of an analog to digital converter and display for the ROLL channel of the present invention.

Referring now to FIG. 10, a portion 240 of the DISPLAY block 40 for the ROLL channel 42 may be seen. The output of the ROLL INTEGRATOR block and circuit 48 is provided on a ROLL INT terminal or line 242. The output of the ROLL AVERAGER block and circuit 50 is provided on a ROLL S/H terminal or line 244. The ROLL INT and ROLL S/H signals are provided to the analog to digital converter integrated circuit 114 which is preferably a TC7106 type 3½ digit A/D converter, available from Microchip Technology, Inc., 2355 West Chandler Blvd., Chandler, Ariz. 85224-6199. The A/D converter 114 contains all the circuitry necessary for analog to digital conversion and also provides decoded outputs for a 3½ digit LCD display. The ROLL S/H signal is provided to the (−) analog input and the ROLL INT signal is provided to the (+) input of the A/D converter 114. The A/D inputs are thus seen to be connected differentially between the NULL reference voltage and the INTEGRATOR output. The A/D converter is preferably scaled to display the output in mechanical degrees of rotation. The least significant digit output provides tenths of degrees and is not used. The three most significant digit outputs provide "degrees, tens of degrees, and 100 degrees" respectively. The digital decoded outputs from the A/D converter are connected to a visually perceptible digital display 18a, preferably a S401C39TR type LCD display available from Lumex, Inc. of 290 East Helen Road, Palatine, Ill. 60067. The digital display 18a simultaneously displays degrees, tens of degrees, 100 degrees, and either a positive or negative sign to indicate direction of rotation from the ZERO condition or position. A 10K ohm potentiometer 248 provides a single system calibration adjustment for the ROLL channel 42.

Figure 11:
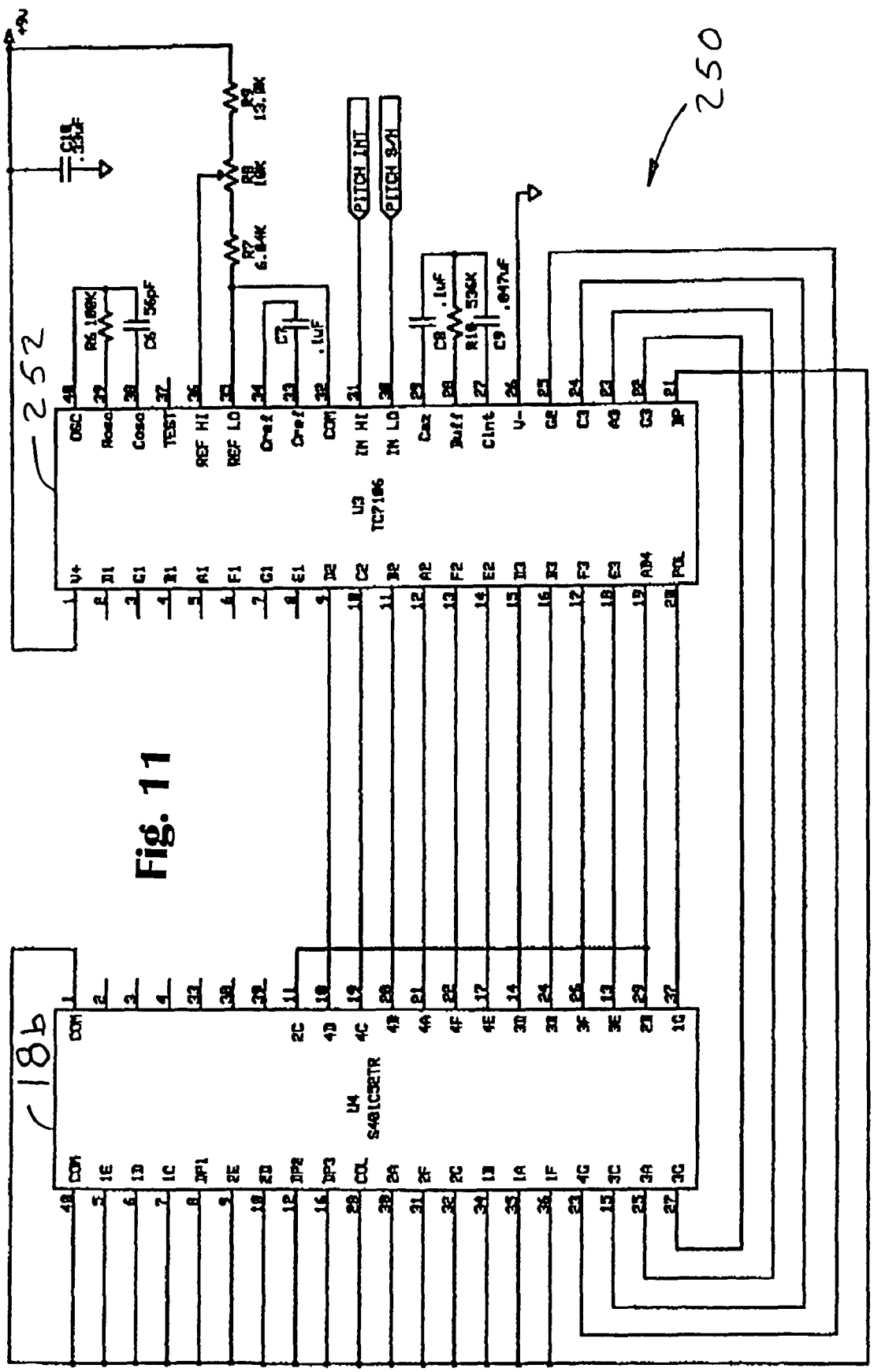
FIG. 11 is a detailed electrical schematic of an analog to digital converter and display for the PITCH channel of the present invention.

Referring now to FIGS. 11 and 12, it may be seen that the PITCH and YAW portions 250 and 260 the DISPLAY block 40 are essentially identical to the ROLL portion 240, each with their own AND converters 252 and 262 and LCD displays 18b and 18c, respectively. It is to be understood that DISPLAY block 40 include the ROLL, PITCH, and YAW displays 18a, 18b, and 18c, and in this embodiment also includes A/D converters 114, 252, and 262.

It is to be understood that the ROLL, PITCH, and YAW data (either in analog or digital form) may be delivered to other circuitry and systems (not shown) in addition to (or as an alternative to) the DISPLAY block 40. For example, the digital data representing the final ROLL, PITCH, and YAW angle selected with respect to the reference plane may be recorded by a data logger (not shown) if desired. Furthermore, it is to be understood that data may be provided in serial form as well as in parallel form, using conventional circuitry to produce serial digital data from either the analog values or parallel digital values.

Figure 13:
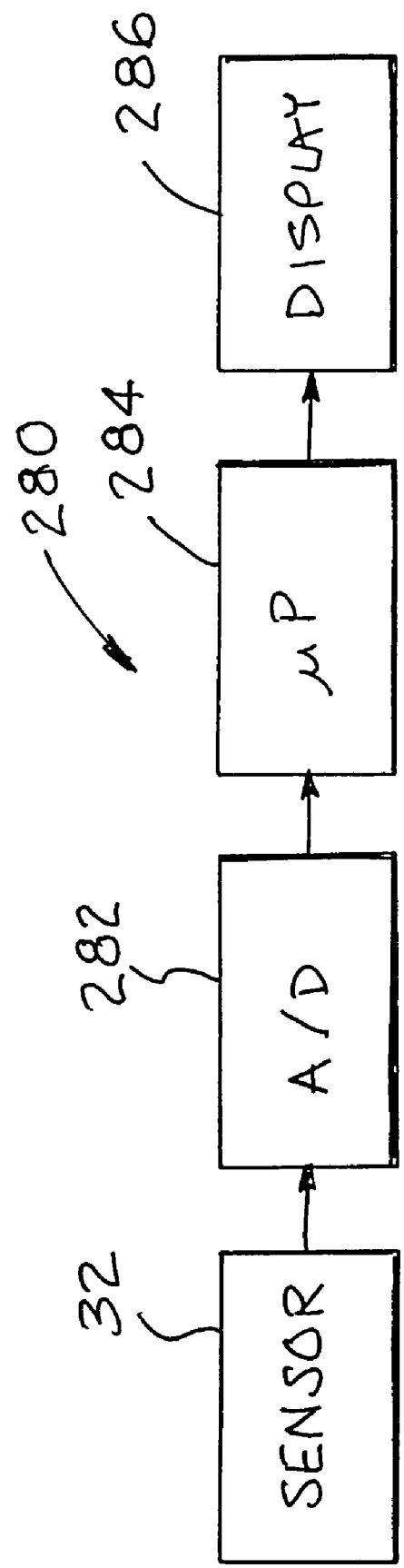
FIG. 13 is a simplified block diagram of an alternative embodiment of the present invention.

Referring now to FIG. 13, an alternative embodiment of the present invention may be seen in a software block diagram 280. In this embodiment, rate sensor 32 has an output that is immediately converted to digital form by an A/D converter 282 (which may be the same or different than A/D converter 114. The A/D converter output is then provided to a microprocessor-based system 284 which delivers the ROLL, PITCH and YAW information to a DISPLAY 286 which may be the same or different than display 40. This embodiment may also provide the ROLL, PITCH and YAW information to other circuitry or systems (not shown).

In the embodiment of the present invention including accelerometers, the device 10 can be utilized independently or in conjunction with gyroscopes or other sensors to provide three dimensional positional orientation with or without angular change for applications such as osteotomies, placing screws in the pedicle, bone cuts/preparation during total joint arthroplasties, disc replacement, and position of tunnels for ligament and tendon repairs. One sensor useful as an accelerometer, either in combination with the gyroscopic sensors, or independently, is an Analog Devices type ADXL103 accelerometer, which may be used in place of device 32 to detect linear acceleration which is then integrated to obtain linear position (which may be replicated in three orthogonal channels along x, y and z axes). With the ADXL103 type devices, it is believed preferable to include the motion sensing and averaging aspects shown and described herein, to remove device-to-device errors, as is done with the gyroscopic type rate sensors. It is to be understood that if an accelerometer is used to obtain linear position information, two integrations (from acceleration to velocity to position) are needed.

In another embodiment, the device 10 further includes additional sensors such as temperature, ultrasonic, and pressure sensors, for measuring properties of biological tissue and other materials used in the practice of medicine or surgery, including determining the hardness, rigidity, and/or density of materials, and/or determining the flow and/or viscosity of substances in the materials, and/or determining the temperature of tissues or substances within materials. Specifically these additional sensors can, for example, identify the margins between cortical and cancellous bone, determine the thickness of cancellous bone, monitor temperature of cement for fixating implants, and differentiate between nucleus pulposis and annulus of a spinal disc. Also, these sensors can identify cracks/fractures in bone during placement of implants such as pedicle screw placement, screw fixation in bone, femoral implant during THA, and identify tissue-nerve margins to determine proximity of nerves.

Figure 14:
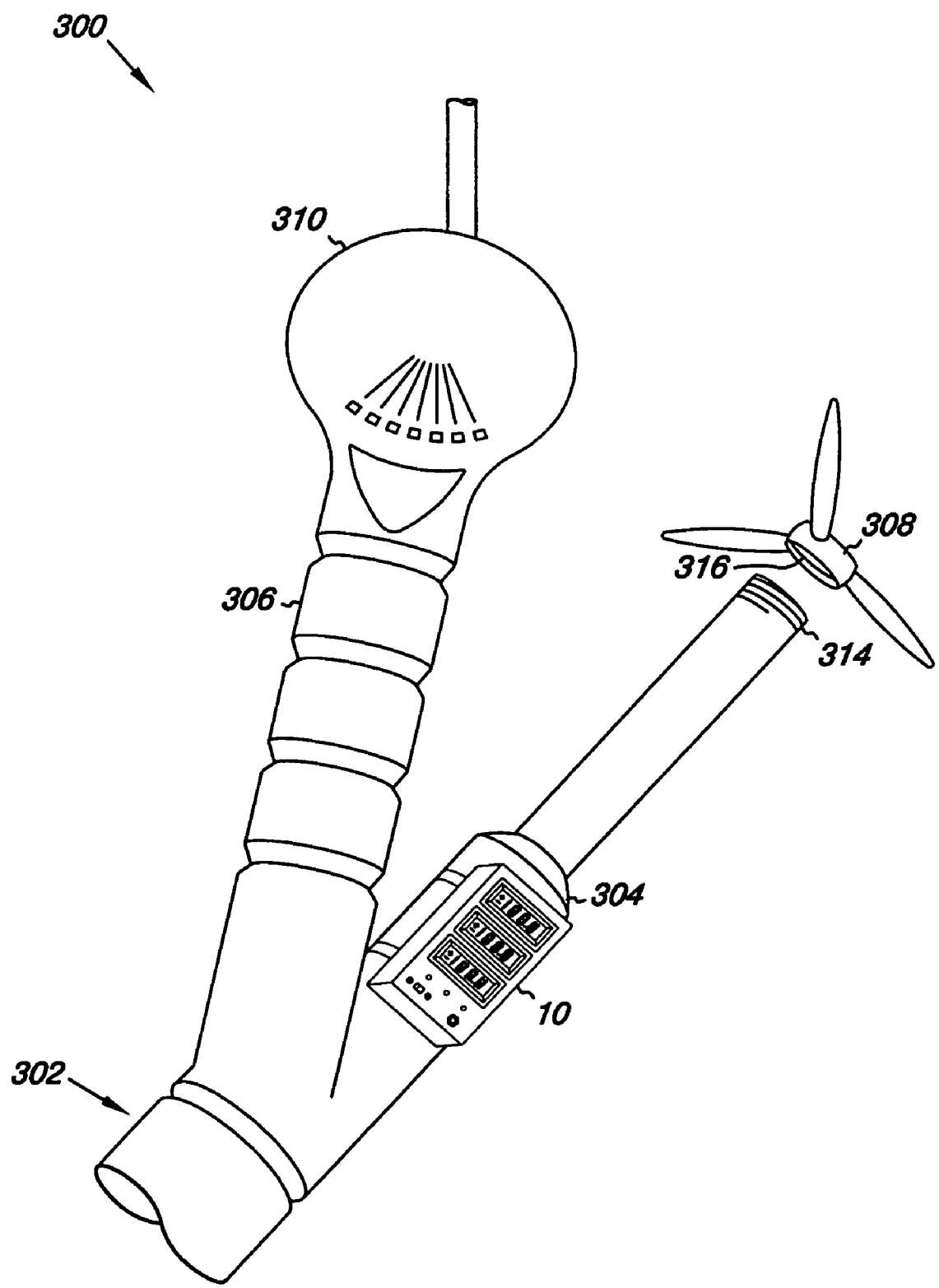
FIG. 14 is a perspective view of an acetabular alignment instrument for use in obtaining a desired orientation for a prosthetic acetabular socket with respect to a patient's acetabulum, according to one embodiment of the present invention.

FIG. 14 shows an acetabular alignment instrument 300 for use in obtaining a desired orientation for a prosthetic acetabular socket with respect to a patient's acetabulum, according to one embodiment of the present invention. The use of such an instrument for orthopaedic hip procedures, such as THR, is well known in the art. One such instrument, for example, is disclosed in U.S. Pat. No. 6,743,235, which is hereby incorporated by reference. The instrument 300 can be any instrument known for the placement and orientation of acetabular components, including the preparation instruments for THR procedures.

As shown in FIG. 14, the instrument 300 includes a handle 302, a prosthetic support shaft 304, an orientation shaft 306, the surgical orientation device 10, and an anatomic benchmark alignment guide 308. As shown, the surgical orientation device 10 is securely attached to the support shaft 304, such that the device 10 moves in concert with the support shaft 304. As further shown in FIG. 14, the orientation shaft 306 includes an orientation guide 310, which may be used by a surgeon for manually orienting an implant or prosthetic. In one embodiment, the instrument 300 does not include an orientation guide 310. The support shaft 304 has external threads 314 at a distal end. The threads 314 are adapted to mate with corresponding internal threads 316 on the alignment guide 308, such that the alignment guide is releasably attachable to the support shaft 304.

Figure 15:
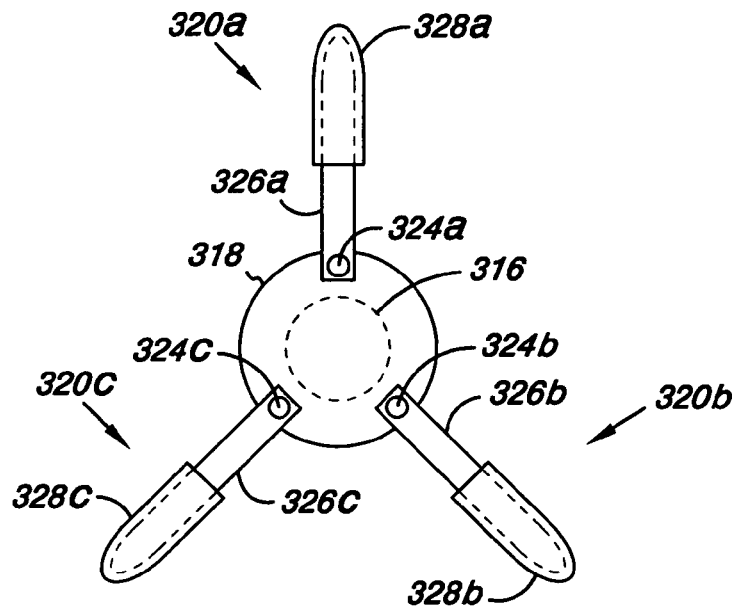
FIG. 15 is a plan view of the top or distal face of the alignment guide shown in FIG. 14.

FIG. 15 is a plan view of the top or distal face of the alignment guide 308. As shown, the alignment guide 308 includes a body portion 318 and wings or arms 320a, 320b, and 320c, which are disposed generally in the same plane. The body portion 318 includes internal threads 316 for mating with the support shaft 304. In one embodiment, the arms 320 secured at points 320 degrees apart around the circumference of the body portion 318 by pivots 324a, 324b, and 324c. The pivots 324 allow for slight in-plane rotation of the arms 320 where necessary, for example to avoid contact with an anatomical aberration as the lip of the acetabulum. In another embodiment, the arms 320 are fixed to the body portion 318 such that they cannot pivot. In a further embodiment, the pivots 324 are located at any point along the arms 320.

As further shown, the arms 320 include an inner arm 326 and an outer arm 328, which are coupled to each other such that the outer arms 328 can telescope or extend with respect to the inner arms 326. This telescoping action allows the surgeon to adjust the length of the arms 320, based on the diameter of a particular patient's acetabulum. In another embodiment, the arms 320 are made from a unitary piece and thus are not amenable to a length adjustment. The distal ends of the arms 320 define an outer diameter of the alignment guide 308. The arms 320, in one embodiment, have a length of from about 40 to about 70 mm, with each arm 320 having the same length. The length of the arms is driven by the diameter of a particular patient's acetabulum, such that the outer diameter of the alignment guide is slightly larger (e.g., 1-3 mm) than the diameter of the acetabulum. In various exemplary embodiments, the arms 320 have a length of 48, 52, 56, 60, or 64 mm. In one embodiment, the arms 320 have a width of from about 2 to about 5 mm and a thickness of from about 1 to about 3 mm. In one exemplary embodiment, the arms have a width of about 3.5 mm and a thickness of about 2 mm.

Figure 16:
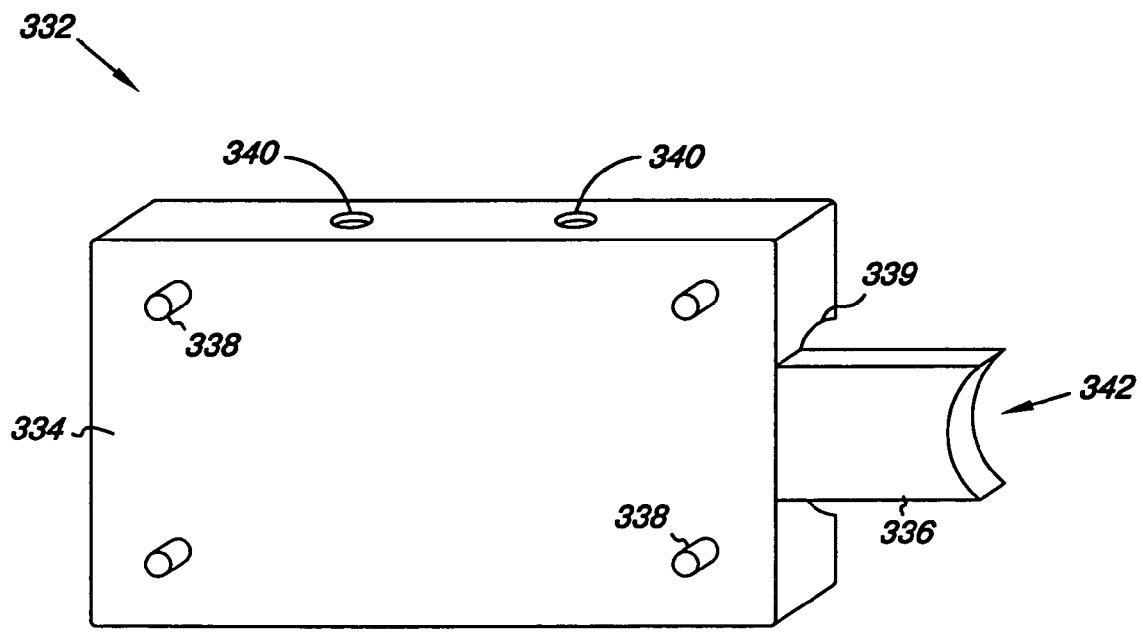
FIG. 16 shows a perspective view of an attachment base for attaching the device to the support shaft 304, according to one embodiment of the present invention.

FIG. 16 shows a perspective view of an attachment base 332 for attaching the device 10 to the support shaft 304. As shown in FIG. 16, the attachment base 332 includes a body 334 and a brace 336. The body 332 is dimensioned to generally mate with the dimensions of the housing 12 of the device 10. In one embodiment, the body 334 includes mounting tabs 338 for mating with the housing 12 and fixing the position of the device 10 with respect to the attachment base 332. In one embodiment, the body 334 includes a groove 339 shaped to mate with the outer surface of the support shaft 304. This configuration increases the surface contact between the attachment bases 332 and the support shaft 304, which enhances fixation of the two components. In one embodiment, the body 334 includes holes 340 for accepting a fastener, such as string, wire, spring wire, a strap, a hook and loop fastener, or any other fastener. The fastener is used to fix the body 334 to the support shaft 304. The brace 336 includes a curve 342 configured to accept the outer surface of the orientation shaft 306. The attachment base 332 is attached to the instrument 300 by placing the body 334 on the support shaft 304 and the curve 342 of the brace 336 against the orientation shaft 306. In this position, the brace 336 resists rotation of the attachment base 332 around the circumference of the support shaft 304.

Figure 17:
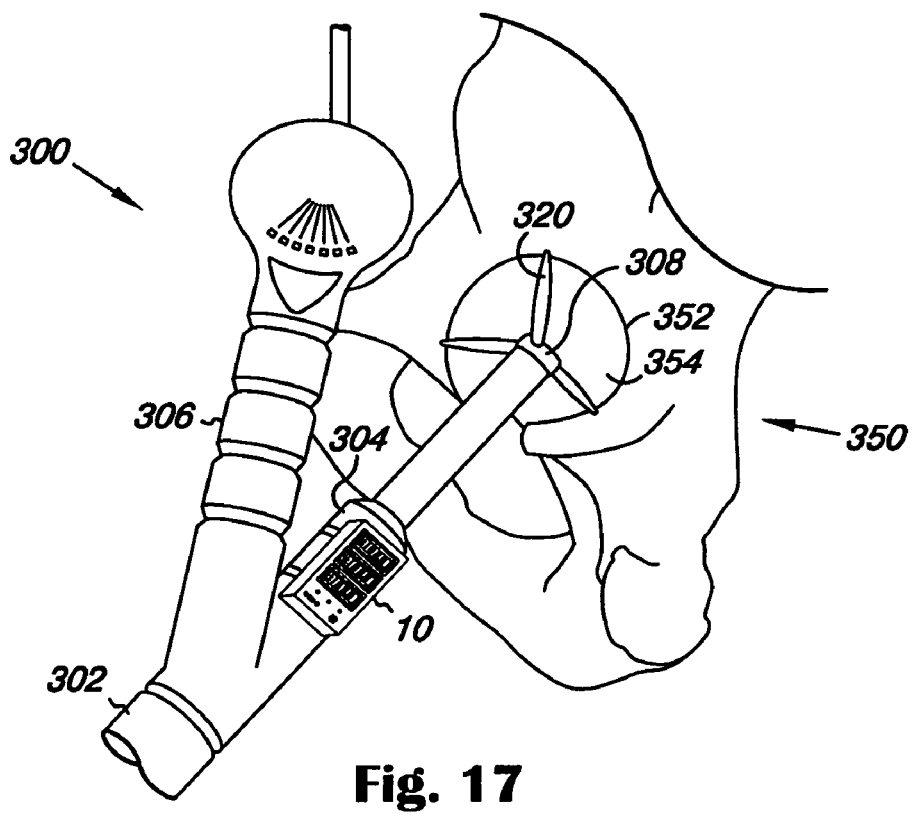
FIG. 17 is a perspective view showing the instrument of FIG. 14 used to identify the plane of the acetabular rim.
Figure 18:
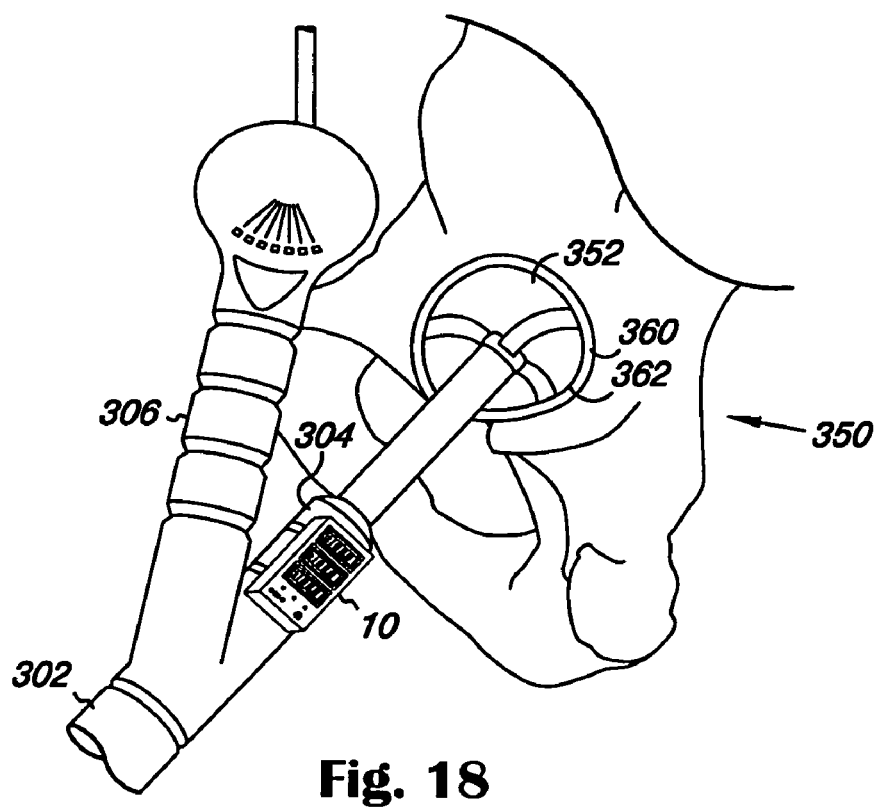
FIG. 18 is a perspective view showing the instrument of FIG. 14 used for positioning an acetabular prosthetic socket.

FIG. 17 shows the instrument 300 during use. As shown, the instrument 300 is in contact with a portion of the pelvic bone 350. Specifically, the alignment guide 308 is contacting the acetabular rim 352 of the acetabulum 354. As shown, the arms 320 have a length sufficient to reach the acetabular rim 352. As shown in FIG. 18, the support shaft 304 is also adapted to mate with a ball support 360, which is used to support an acetabular prosthetic socket 362.

Figure 19A:
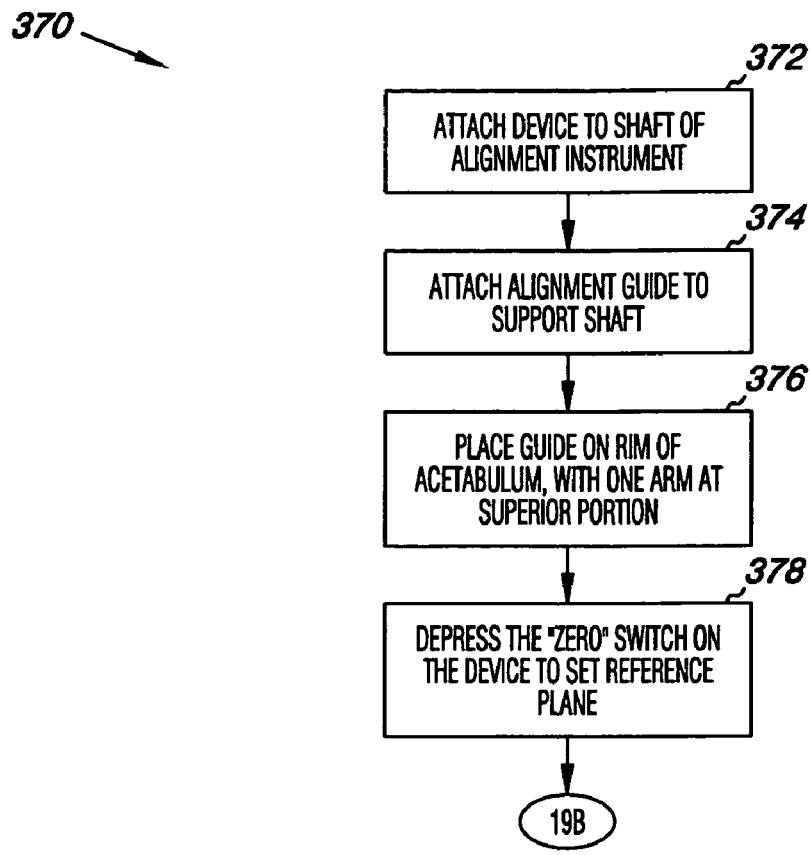
FIGS. 19A and 19B are flow charts illustrating operation of an alignment instrument for orientation of an acetabular prosthetic socket.
Figure 19B:
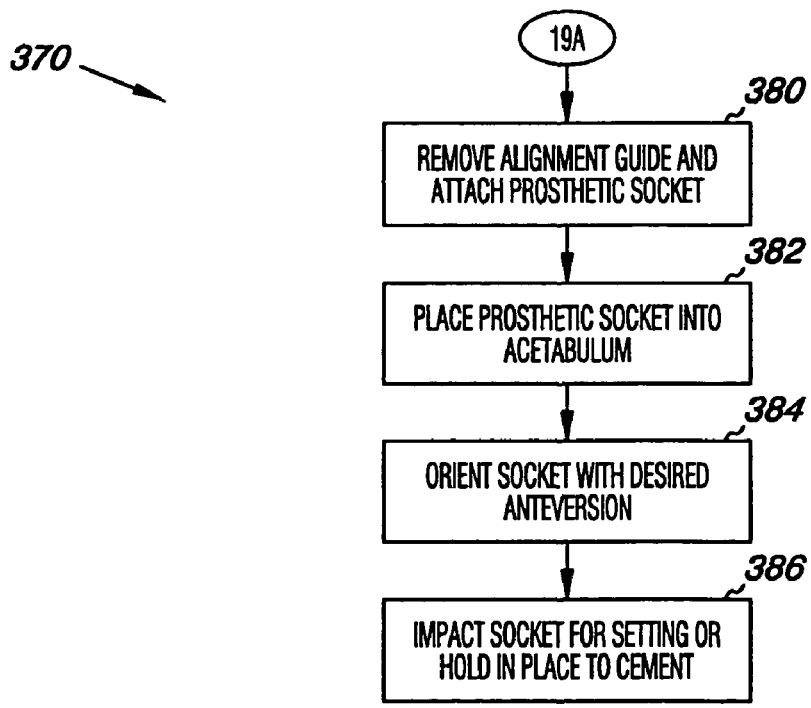

FIG. 19 is a flowchart illustrating an acetabular alignment process 370 for using the alignment instrument 300 to orient an acetabular prosthetic socket 362. As shown, the process 370 includes powering on the device using the power switch 14 and attaching the device to the shaft of the alignment instrument 300 (block 372). The alignment guide 308, having the appropriate diameter, is then attached to the end of the support shaft 304 (block 374). After preparation of the surgical site according to standard procedures, the instrument 300 is placed into the surgical site, such that the alignment guide 308 is resting on the rim 352 of the acetabulum 354 (block 376). In one embodiment, the center of the alignment guide 308 is generally aligned with the center of the acetabulum 354 and the arms are place on the rim 352 of the acetabulum 354, as follows. A first arm is placed on the most superior point of the acetabulum, a second arm is positioned at the lowest point of the acetabular sulcus of the ischium, and a third arm is positioned at the saddle point at the confluence between the illiopubic eminence and the superior pubic ramus. In the absence of a significant acetabular rim, the above anatomic landmarks may be used to identify the plane of the acetabulum.

According to one embodiment, as described above, the arms 320 are adjusted in length by the surgeon using a telescoping action. In another embodiment, the surgeon may need to pivot the arms 320 to avoid an osteophyte or other surface aberration on the rim 352 of the acetabulum 354. Once the alignment guide 308 is correctly positioned on the rim 352 of the acetabulum, the surgeon depresses the zero button 20 to set the reference plane (block 378).

After zeroing the device 10, the surgeon removes the instrument 300 from the surgical patient's body. The alignment guide is then removed and the ball support 360 and prosthetic socket 362 are attached to the support shaft 304 (block 380). The surgeon then places the prosthetic socket 362 into the acetabulum 354 using the instrument 300 (block 382). The surgeon then manipulates the orientation of the prosthetic socket 362 in the acetabulum 354 using the instrument 300, until the device 10 indicates the desired orientation (block 384). In one embodiment, for example, the surgeon manipulates the instrument 300 until the displays 18 on the device indicate an anteversion of 25 degrees. In this embodiment, the ROLL display 18a indicates "25" and the PITCH display 18b and YAW display 18c indicate zero. Next the prosthetic socket 362 is secured to the acetabulum 354 (block 386).

In other embodiments, the device 10 is used on other acetabular instruments to identify the orientation of the instrument with respect to a previously set plane of the acetabulum. When the implant is in the neutral position the information provided by the device may, for example, be in the form of angular measurements to identify information such as rotation, abduction and version angles. In the embodiment of the present invention that includes accelerometers or other sensors for providing linear positioning information, the device 10 also provides information on position changes in linear dimensions to identify properties such as depth of insertion and changes in center of rotation. The instrument 300, including the device 10 is capable of sub-millimeter and sub-degree accuracy to monitor the position and angle with reference to the pelvis. It can provide continuous measurements of cup abduction and flexion angles. These angles may be provided during placement of the preparation instruments, the insertion of the implant, after it is placed and, if needed, after placement of supplementary screws.

Figure 20:
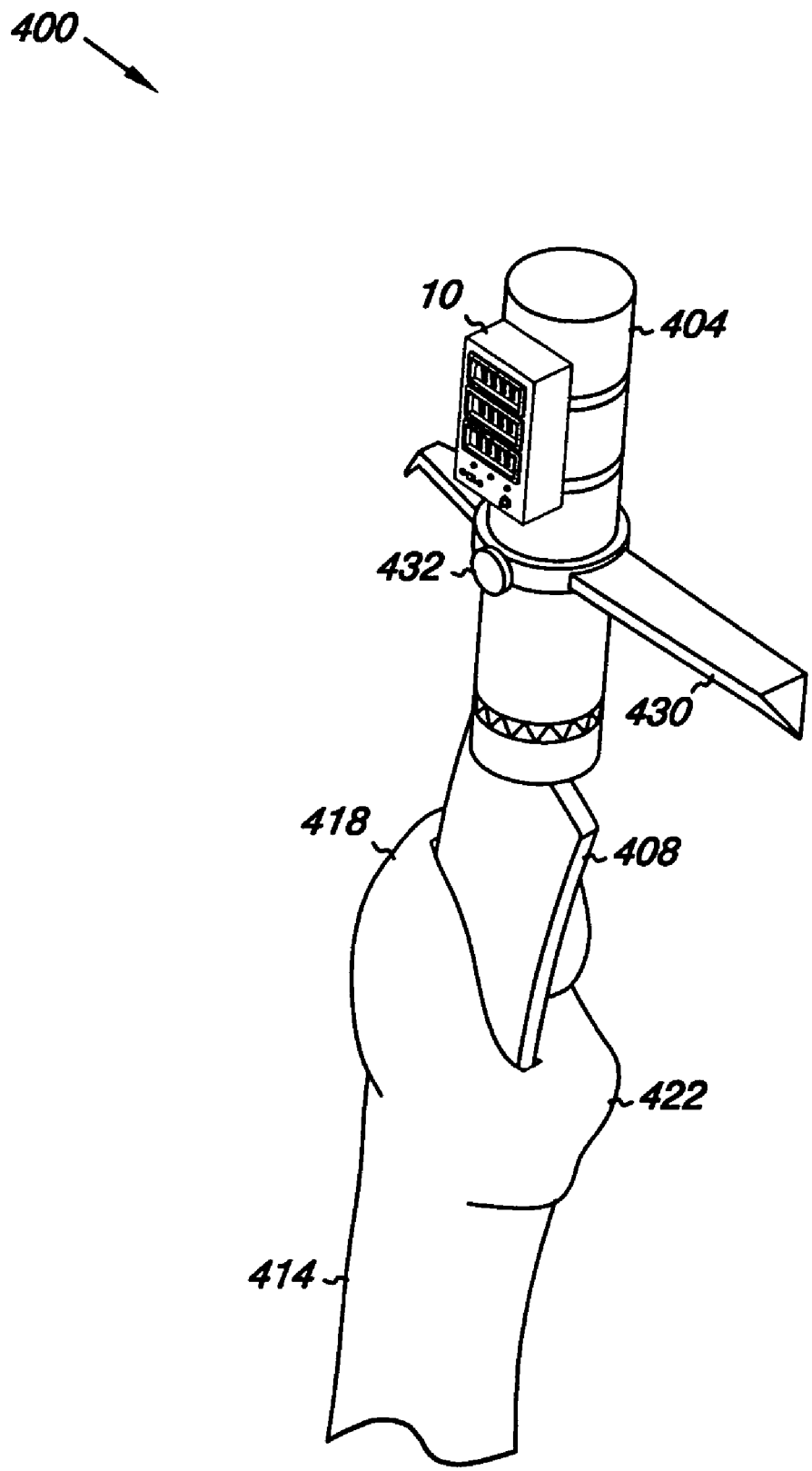
FIG. 20 shows a femoral broaching instrument adapted for aligning the femoral broach with the greater and lesser trochanter of the proximal femur.

FIG. 20 shows a femoral implant instrument 400 for aligning the femoral implant with the greater and lesser trochanter of the proximal femur. The instrument 400 may be, for example, a femoral implant insertion instrument, a femoral rasp, or a femoral broaching instrument. As shown in FIG. 20, the instrument 400 includes a handle 404, a rasp or broach 408, a femoral alignment guide 430, and the device 10. The instrument 400 is used to clear and shape the cancellous bone surrounding the canal of the proximal femur 414. The broach 408 is releasably coupled to the handle 404, such that the surgeon can readily change the broach 408 to one of a different size. The broach 408 is shown in FIG. 20 with the cutting segment embedded in the femur 414. In one embodiment, the instrument 400 is a femoral broaching instrument such as Broach Handle #4700-RH02, available from Wright Medical Technology, Inc. of Arlington, Tenn. In other embodiments, the broach 408 is any other rasp or broach known in the art. As shown, the guide 430 is placed on the body 404 at the desired reference point and attached using the locking mechanism 432. As further explained below, the surgeon may use the guide 430 by aligning it with the greater trochanter 418 and the lesser trochanter 422 at a proximal end of the femur 414.

Figure 21A:
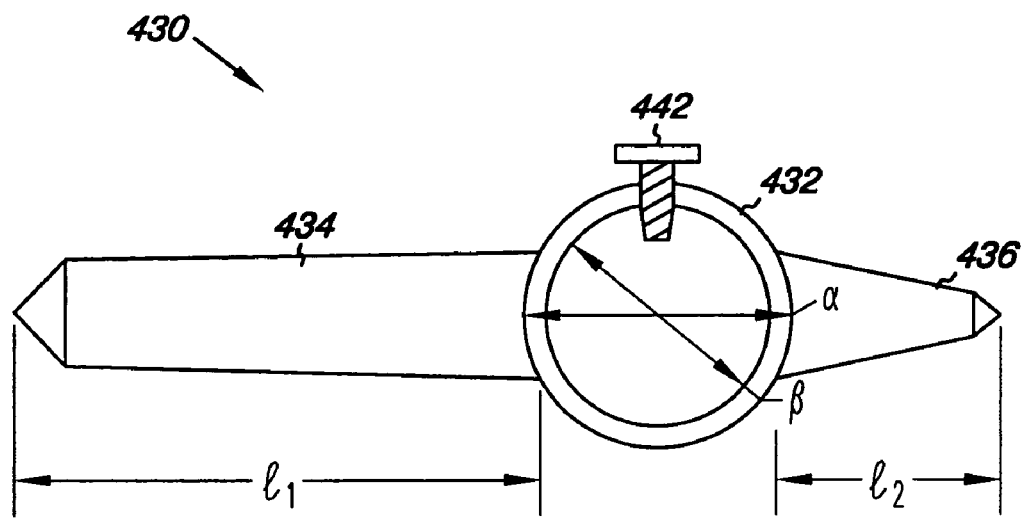
FIGS. 21A and 21B are top and side plan views of a femoral alignment guide.
Figure 21B:
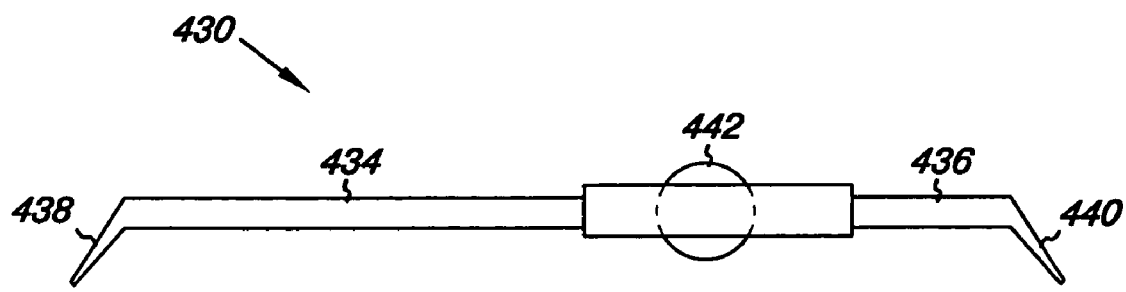

FIGS. 21A and 21B are top and side plan views of a femoral alignment guide 430. As shown, the guide 430 includes a mounting ring 432, a lesser trochanter alignment arm 434, and a greater trochanter alignment arm 436. The alignment arms 434 and 436 extend in generally opposing directions from the mounting ring 432. As shown in FIG. 21B, the alignment arms 434 and 436 include angles ends 438 and 440, respectively. The angled ends 438 and 440 are usable by the surgeon to align the guide 430 with respect to the patient's anatomy. The mounting ring 432 includes a locking screw 442 for securing the guide 430 to the instrument 400. In one exemplary embodiment, the greater trochanter alignment arm 436 has a length ($l_2$) of about 40 percent of a length of the lesser trochanter alignment arm 434. In one embodiment, the lesser trochanter alignment arm 434 has a length ($l_1$) of between about 85 and about 105 mm. In one embodiment, the alignment arm 434 has a length ($l_1$) of about 95 mm. In one embodiment, the mounting ring 432 has an internal diameter ($\beta$) of between about 35 and 45 mm. The specific dimensions of the alignment guide will depend upon the size of the handle 404 and the patient's proximal femur 414.

The femoral alignment guide 430 is used to align the femoral implant by referencing the lesser and greater trochanter of the proximal end of the femur. The guide 430 can also be used to mark the lesser or greater trochanter, or any other point marked by the surgeon, to fix the predetermined/measured angle of the preparation instruments or implant. The surgeon may then move the femur without disrupting his measurement of the chosen anteversion. In one embodiment, the guide 430 is attached to a femoral broaching instrument. The guide 430 is placed at the desired angle and the device 20 is set to zero. For example, the guide 430, in one embodiment, is generally aligned with a center of the greater trochanter 418 and the lesser trochanter 422. The surgeon then turns the instrument 400 to the desired anteversion (e.g., 10 degrees), by using the ROLL display 18a of the device 10. The surgeon then loosens the guide 430, rotates it such that the arms 434 and 436 are again generally aligned with the greater trochanter 418 and the lesser trochanter 422, and secures the guide 430 to the handle 404. The surgeon then drives the instrument 400 into the canal at this orientation and repeats this procedure with a larger broach 408, as needed, using the guide 430 to achieve the desired alignment.

The present invention is also useful in assisting a surgeon with a TSR procedure. In a shoulder replacement, one of the steps is placing a glenoid implant into the glenoid of the patient's scapula. One such glenoid implant is described in U.S. Pat. No. 6,679,916, which is hereby incorporated by reference. Another step of the TSR procedure is placement of the humeral implant. The device 10 of the present invention is useful for assisting a surgeon in achieving proper orientation of the glenoid implant with respect to the glenoid vault and for achieving proper orientation of the humeral implant. The device 10, for example, can be attached to a T-handle or a drill commonly used by the surgeon with the glenoid planer. The device 10, in further embodiment, can be attached to a tapered reamer used for reaming the humeral canal or to a humeral head cutting guide.

Figure 22A:
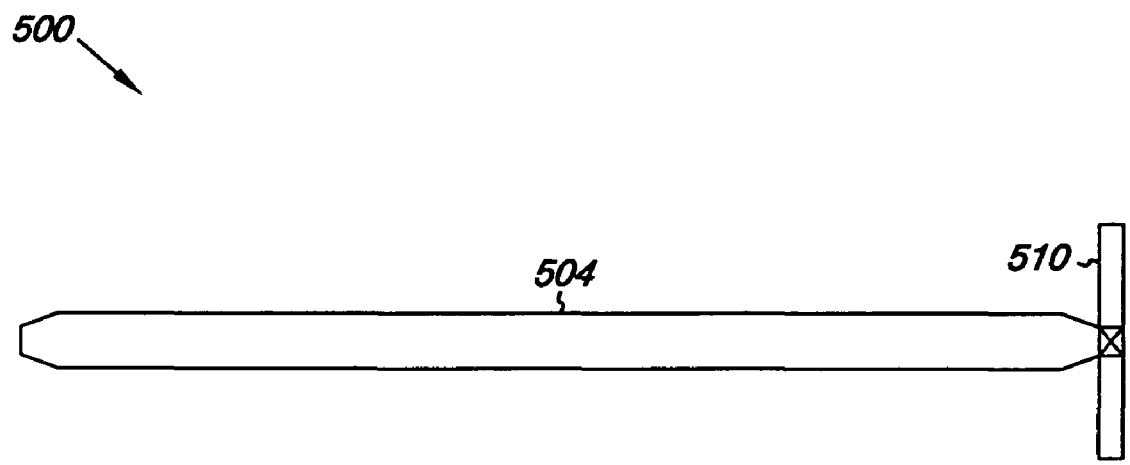
FIGS. 22A and 22B are a side plan view and a front plan view of an implant instrument and alignment guide for identifying the plane of the glenoid during a TSR procedure.
Figure 22B:
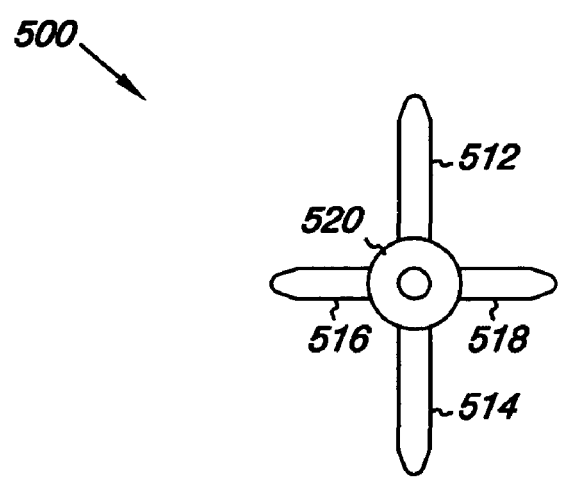

FIG. 22A shows a side plan view of a glenoid implant insertion instrument 500 for use in orientation of a glenoid implant. As shown, the insertion instrument 500 includes a shaft 504 and an alignment guide 510. FIG. 22B shows a front plan view of the alignment guide 510. As shown, the alignment guide 510 includes an upper arm 512, a lower arm 514, an anterior arm 516, and a posterior arm 518, which are attached to a hub 520. The arms are sized such that they span the glenoid rim for a particular patient.

Figure 23:
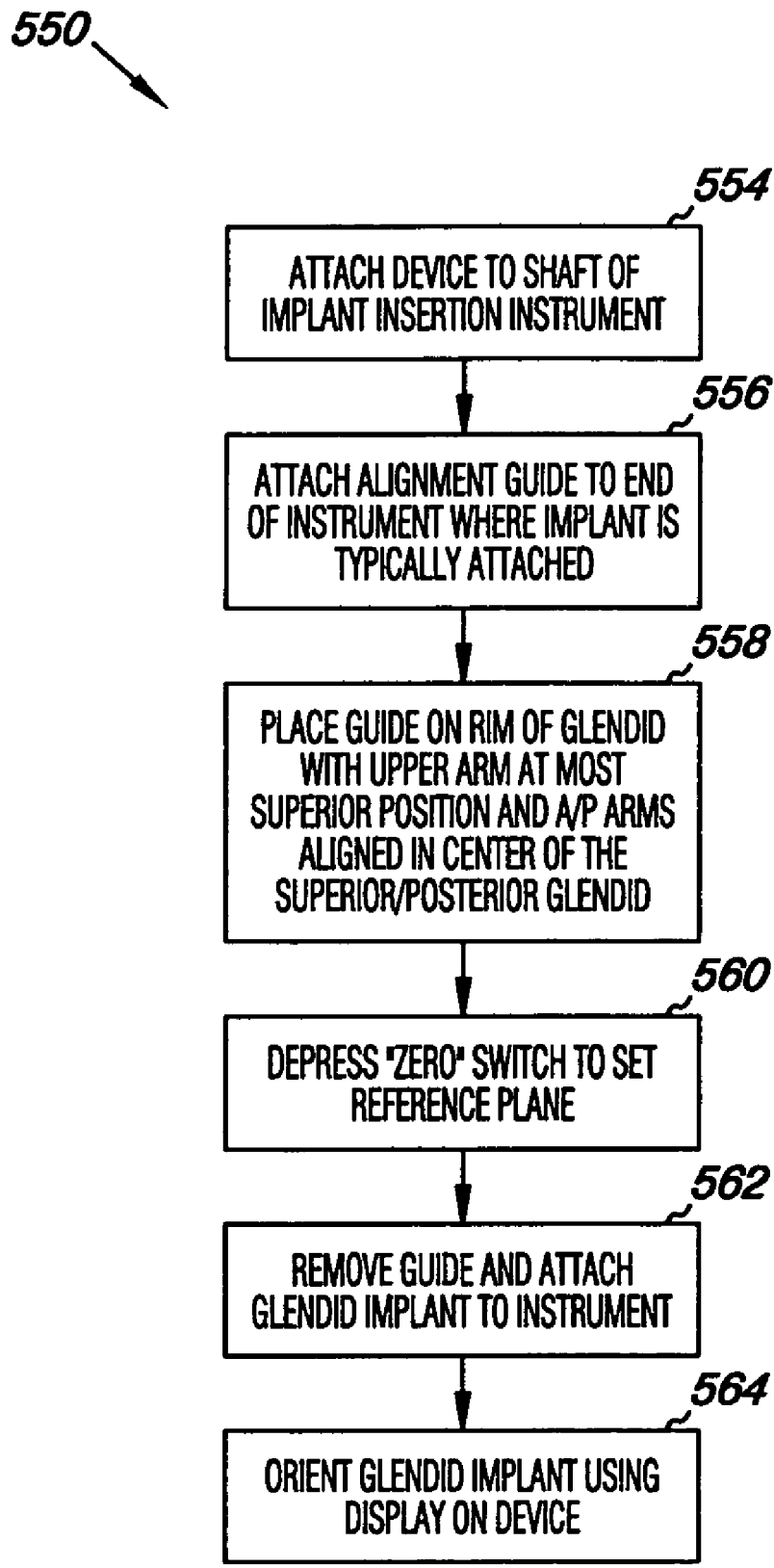
FIG. 23 is a flowchart describing the use of the alignment guide of FIG. 22.

FIG. 23 is a flowchart illustrating a glenoid implant alignment process 550 for using the implant insertion instrument 500 to orient a glenoid implant. As shown, the process 550 includes securely attaching the device 10 to the shaft of an implant insertion instrument 500 or glenoid planing instrument (block 554). The alignment guide 510 is attached to the end of the instrument where the glenoid implant is normally attached (block 556). The guide 510 is placed on the rim of the glenoid, such that the upper arm is placed at the most superior position of the rim, and the anterior and posterior arms are generally aligned in the center of the superior/posterior glenoid (block 558). Again, the arms may be adjusted to avoid significant osteophytes. The "zero" switch is then depressed to set the displays 18 on the device 10 to zero, which sets the reference plane (block 560). The alignment guide 510 is removed and the glenoid implant is attached to the insertion instrument 500 (block 562). Finally, the surgeon uses the displays 18 on the device 10 to achieve desired orientation and/or positioning of the glenoid implant (block 564). The surgeon then fixes the glenoid implant in the desired location.

Figure 24:
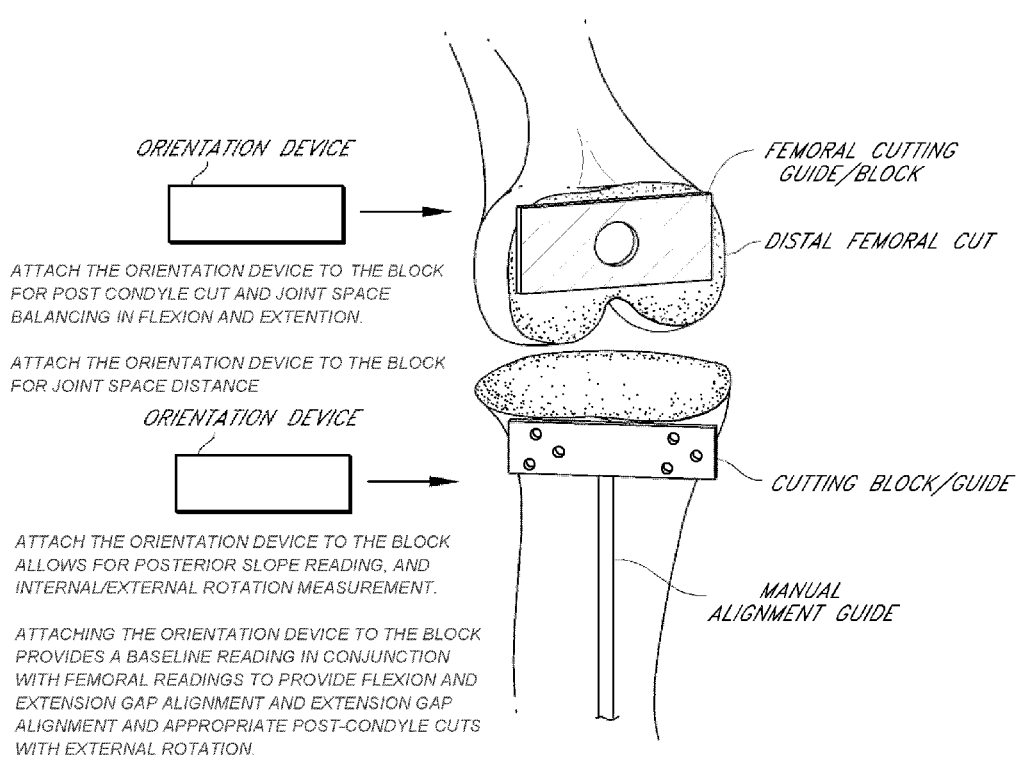
FIG. 24 is a schematic diagram of a system for use in a knee procedure.

In yet another embodiment, the device 10 is used by a surgeon to facilitate TKA. For TKA, the device 10 may be affixed to the initial guides commonly used by surgeons, to enable more accurate alignment than that provided by the existing guides. In various exemplary embodiments, the device 10 can be affixed to the cutting blocks to provide more accurate rotational alignment, varus/valgus alignment, and level of resection. See FIG. 24. The device 10 can also be affixed to any other instruments known in the art and commonly employed in a TKA procedure.

With respect the instruments described above, which include sensors for providing orientation and/or position information, the sensors may include a sensor configured to make a measurement related to the at least one property at multiple locations on or in the instrument or implant. According to one embodiment, the sensor includes a plurality or an array of sensors to measure one or more properties over multiple points, angles, distance, areas, or any combination thereof.

Various modifications and additions can be made to the exemplary embodiments discussed without departing from the scope of the present invention. Accordingly, the scope of the present invention is intended to embrace all such alternatives, modifications, and variations as fall within the scope of the claims, together with all equivalents thereof.

We claim:

1. A system for preparing a knee structure of a patient to receive a medical implant and for aligning the implant with respect to an anatomical location in the patient, the system comprising:

a first instrument configured to engage at least a portion of the knee structure of the patient and to be oriented with respect to the anatomical location, the first instrument configured to prepare the knee structure to receive the implant, the anatomical location relating to a knee joint location near the proximal portion of the tibia and the distal portion of the femur, the first instrument comprising:

an elongate alignment guide for aligning the tibia with respect to the anatomical location;

a cutting block coupled to the alignment guide, the cutting block configured to engage at least the proximal portion of the tibia;

a proximal portion for engaging the knee joint location; and a distal portion;

a second instrument configured to engage at least a distal portion of the femur and to be oriented with respect to the anatomical location; and a surgical orientation device attached to the first instrument and configured to be selectively attachable and detachable with the first instrument and the second instrument, the surgical orientation device when detached being a hand-held, stand alone device having an internal reference frame for placing the proximal portion of the tibia or the distal portion of the femur in a desired position with respect to the anatomical location, the orientation device comprising:

a housing containing a plurality of electronic components, the components comprising:

at least one sensor for providing a signal corresponding to angular position of the orientation device;

a microprocessor in communication with the at least one sensor and programmed to calculate, using at least the signal and the reference frame, a first angle of the surgical orientation device relative to a first axis and a second angle of the surgical orientation device relative to a second axis;

a display electronically coupled to the microprocessor for displaying the first and second angles when the surgical orientation device is attached to the first or second instrument, and a zeroing device for re-setting the surgical orientation device relative to the reference frame.

2. The system for preparing a knee structure of claim 1, wherein the cutting block is disposed at a proximal portion of the first instrument.

3. The system for preparing a knee structure of claim 1, wherein the second instrument comprises a distal femoral cutting block configured to be coupled with the surgical orientation device to a distal portion of a femur.

4. The system for preparing a knee structure of claim 3, wherein the distal femoral cutting block is configured to be coupled with a distal end of the femur after a condyle cut.

5. The system for preparing a knee structure of claim 1, wherein the at least one sensor comprises a gyroscopic sensor.

6. The system for preparing a knee structure of claim 1, wherein the surgical orientation device is coupled with a proximal portion of the first instrument to provide flexion and extension gap alignment.

7. The system claim 1, wherein the cutting block is disposed at a proximal end of the first instrument or the alignment guide.

8. The system of claim 1, wherein the at least one sensor comprises an accelerometer.

9. The system of claim 1 wherein the alignment guide is movably coupled to the first instrument.

10. The system of claim 1 wherein the surgical orientation device is configured to align the tibia to a desirable degree of varus/valgus.

11. The system of claim 1 wherein the surgical orientation device is configured to align the tibia to a desirable degree of posterior slope.

12. The system of claim 1, wherein the display comprises numeric representations representing numbers of degrees of alignment.

13. The system of claim 1 wherein the second instrument comprises a second cutting block.

* * * * *